(12) United States Patent
Hausdorff et al.

(10) Patent No.: US 9,981,035 B2
(45) Date of Patent: May 29, 2018

(54) PROCESS FOR PREPARING PNEUMOCOCCAL POLYSACCHARIDE-PROTEIN CONJUGATES

(71) Applicant: Wyeth LLC, New York, NY (US)

(72) Inventors: William P. Hausdorff, Brussels (BE); George Rainer Siber, New York, NY (US); Peter R. Paradiso, Radnor, PA (US)

(73) Assignee: Wyeth LLC, New York, NY (US)

( * ) Notice: Subject to any disclaimer, the term of this patent is extended or adjusted under 35 U.S.C. 154(b) by 0 days. days.

(21) Appl. No.: 15/042,189

(22) Filed: Feb. 12, 2016

(65) Prior Publication Data

US 2016/0158345 A1 Jun. 9, 2016

Related U.S. Application Data

(63) Continuation of application No. 14/322,057, filed on Jul. 2, 2014, now Pat. No. 9,399,060, which is a continuation of application No. 13/439,111, filed on Apr. 4, 2012, now Pat. No. 8,808,708, which is a continuation of application No. 12/357,853, filed on Jan. 22, 2009, now Pat. No. 8,895,024, which is a continuation of application No. 11/395,593, filed on Mar. 31, 2006, now abandoned.

(60) Provisional application No. 60/669,605, filed on Apr. 8, 2005.

(51) Int. Cl.
| | |
|---|---|
| A61K 39/09 | (2006.01) |
| A61K 39/385 | (2006.01) |
| A61K 47/00 | (2006.01) |
| A61K 39/39 | (2006.01) |
| A61K 47/64 | (2017.01) |
| A61K 39/00 | (2006.01) |

(52) U.S. Cl.
CPC .......... *A61K 39/385* (2013.01); *A61K 39/092* (2013.01); *A61K 39/39* (2013.01); *A61K 47/646* (2017.08); *A61K 2039/55505* (2013.01); *A61K 2039/6031* (2013.01); *A61K 2039/6037* (2013.01); *A61K 2039/70* (2013.01)

(58) Field of Classification Search
CPC .......... A61K 2039/6037; A61K 39/092; C08B 37/006
See application file for complete search history.

(56) References Cited

U.S. PATENT DOCUMENTS

| | | | |
|---|---|---|---|
| 4,097,666 A | 6/1978 | Johnson et al. | |
| 4,673,574 A | 6/1987 | Anderson | |
| 4,902,506 A | 2/1990 | Anderson et al. | |
| 5,097,020 A | 3/1992 | Anderson et al. | |
| 5,153,312 A | 10/1992 | Porro | |
| 5,306,492 A | 4/1994 | Porro | |
| 5,623,057 A | 4/1997 | Marburg et al. | |
| 6,248,570 B1 | 6/2001 | Michon et al. | |
| 6,620,928 B2 | 9/2003 | Besemer | |
| 7,018,637 B2 | 3/2006 | Chong et al. | |
| 7,582,459 B2 | 9/2009 | Hamidi et al. | |
| 7,588,765 B2 | 9/2009 | Porro | |
| 7,709,001 B2 | 5/2010 | Hausdorff et al. | |
| 7,955,605 B2 | 6/2011 | Prasad | |
| 2001/0048929 A1 | 12/2001 | Chong et al. | |
| 2003/0147922 A1 | 8/2003 | Capiau et al. | |
| 2003/0180316 A1 | 9/2003 | Boutriau et al. | |
| 2004/0096461 A1 | 5/2004 | Michon et al. | |
| 2004/0170638 A1* | 9/2004 | Mistretta | A61K 39/092 424/184.1 |
| 2004/0202668 A1 | 10/2004 | Boutriau et al. | |
| 2004/0213817 A1 | 10/2004 | Miller et al. | |
| 2006/0165730 A1 | 7/2006 | Porro | |
| 2006/0228380 A1 | 10/2006 | Hausdorff et al. | |
| 2007/0110762 A1 | 5/2007 | Jessouroun et al. | |
| 2007/0184071 A1 | 8/2007 | Prasad et al. | |
| 2007/0231340 A1 | 10/2007 | Hausdorff et al. | |
| 2009/0130137 A1 | 5/2009 | Hausdorff et al. | |
| 2010/0316666 A1 | 12/2010 | Hausdorff et al. | |
| 2011/0071279 A1 | 3/2011 | Hausdorff et al. | |

(Continued)

FOREIGN PATENT DOCUMENTS

| | | |
|---|---|---|
| EP | 0477508 | 4/1992 |
| EP | 0 497 525 A2 * | 8/1992 |
| EP | 0497524 B1 | 7/1998 |

(Continued)

OTHER PUBLICATIONS

SK Chemicals Co., Ltd, "Brief", Case No. 2013 Dang 2673 (Patent Invalidation Action against KR 1298053), 28 pages, dated Jun. 20, 2014 (English Translation only).

(Continued)

*Primary Examiner* — Padmavathi Baskar
(74) *Attorney, Agent, or Firm* — Keith D. Hutchinson; Matthew J. Pugmire

(57) ABSTRACT

An immunogenic composition having 13 distinct polysaccharide-protein conjugates and optionally, an aluminum-based adjuvant, is described. Each conjugate contains a capsular polysaccharide prepared from a different serotype of *Streptococcus pneumoniae* (1, 3, 4, 5, 6A, 6B, 7F, 9V, 14, 18C, 19A, 19F and 23F) conjugated to a carrier protein. The immunogenic composition, formulated as a vaccine, increases coverage against pneumococcal disease in infants and young children globally, and provides coverage for serotypes 6A and 19A that is not dependent on the limitations of serogroup cross-protection.

4 Claims, 3 Drawing Sheets

(56) References Cited

U.S. PATENT DOCUMENTS

| | | |
|---|---|---|
| 2011/0201791 A1 | 8/2011 | Prasad |
| 2012/0237542 A1 | 9/2012 | Hausdorff et al. |

FOREIGN PATENT DOCUMENTS

| | | |
|---|---|---|
| EP | 0497525 B1 | 8/1998 |
| EP | 1035137 | 9/2000 |
| FR | 2857364 | 1/2005 |
| WO | 92/19265 A1 | 11/1992 |
| WO | 93/13202 A1 | 7/1993 |
| WO | 97/041731 A1 | 11/1997 |
| WO | 98/51339 | 11/1998 |
| WO | 99/42130 | 8/1999 |
| WO | 2000/017370 | 3/2000 |
| WO | 00/18434 A1 | 4/2000 |
| WO | 00/56358 A2 | 9/2000 |
| WO | 00/56359 A2 | 9/2000 |
| WO | 00/62801 A2 | 10/2000 |
| WO | 02/00249 A2 | 1/2002 |
| WO | 02/22167 A2 | 3/2002 |
| WO | 02/098368 A2 | 12/2002 |
| WO | 02/098369 A2 | 12/2002 |
| WO | 2003/051392 | 6/2003 |
| WO | 03/063766 A2 | 8/2003 |
| WO | 2004/011027 A1 | 2/2004 |
| WO | 2004/067574 | 8/2004 |
| WO | 2004/094596 A2 | 11/2004 |
| WO | 2005/058940 A2 | 6/2005 |
| WO | 2006/110381 A1 | 10/2006 |
| WO | 2011/100151 A1 | 8/2011 |

OTHER PUBLICATIONS

Strawman Limited, "Response to Patentee's Observations Dated Aug. 2, 2013 and Patentee's Written Submissions Dated Aug. 13, 2014", Opposition Against European Patent 1 868 645, 24 pages, submitted Aug. 25, 2014.
Wyeth LLC, "Additional Written Submissions in Preparation of Oral Proceedings", Opposition Against European Patent No. EP1868645, 14 pages submitted Oct. 14, 2014.
Wyeth LLC, "Response", Case No. 2013 Dang 2673 (Invalidation Action Against Korean Patent No. 1298053), 20 pages, submitted Sep. 30, 2014 (English Translation Only).
Wyeth LLC, "Written Submissions Following the Communication Pursuant to Rule 115(1) EPC dated Jan. 31, 2014", Opposition Against European Patent No. EP1868645, 14 pages submitted Aug. 13, 2014.
Zimmer, F.J., "In Response to the Summons to Attend Oral Proceedings Pursuant to Rule 115(1) EP dated Jan. 31, 2014", Opposition Against European Patent No. 1 868 645, 16 pages, submitted Aug. 25, 2014.
Indian Patent Office, "First Examination Report", Indian Patent Application No. 8081/DELNP/2007, 5 pages, dated Jun. 17, 2013.
Panacea Biotec Ltd., "Opponent Panacea Biotec's Response to Wyeth's Arguments Dated Jun. 17, 2014 and Sep. 17, 2013", Indian Patent Application No. 8081/DELNP/2007, 28 pages, dated Dec. 18, 2014.
Wyeth LLC, "Written Submission in Relation to 8081/DELNP/2007", Indian Patent Application No. 8081/DELNP/2007, 111 pages, dated Jul. 13, 2015.
Zimmer, F.J., "In Response to Patentee's Written Submission of Aug. 13, 2014", Opposition Against European Patent No. 1 868 645, 11 pages, submitted Oct. 1, 2014.
SK Chemicals Co., Ltd, "Brief", Case No. 2013 Dang 2673 (Invalidation Action Against Korean Patent No. 1298053), 23 pages, submitted Apr. 27, 2015 (English Translation Only).
SK Chemicals Co., Ltd, "Brief II", Case No. 2015 Heo 4613 (Patent Invalidation Action against KR 1298053), 26 pages, dated Sep. 24, 2015 (Extended Summarized English Translation only).
Wyeth LLC, "Response", Case No. 2015 Heo 4613 (Patent Invalidation Action), 44 pages, submitted Nov. 2, 2015 (English Translation Only).
SK Chemicals Co., Ltd, "Brief", Case No. 2015 Heo 4613 (Patent Invalidation Action), 8 pages, submitted Jan. 28, 2016 (English Translation Only).
Xiaohan Zhu, "Request for Invalidation of Patent Rights", Chinese Patent No. ZL 200680017776.8, 10 pages, received Oct. 15, 2014 (English Translation Only).
Wyeth LLC, "Response to the Invalidation Request", Chinese Patent No. ZL 200680017776.8, 15 pages, submitted Nov. 28, 2014 (English Translation Only).
Fengjie Qiao, "Observations", Invalidation Action against Chinese Patent No. ZL 200680017776.8, 22 pages, submitted on Jan. 14, 2015 (English translation only).
Wyeth LLC, "Response", Invalidation Action against Chinese Patent No. ZL 200680017776.8, 18 pages, submitted on Mar. 9, 2015 (English translation only).
Patent Examination Board, "Examination Decision on Request for Invalidation", Invalidation Action against Chinese Patent No. ZL 200680017776.8, 17 pages, dated Jul. 15, 2015 (English translation only).
Seiji Takahashi, "Submission of Publications", Third Party Submission in Japanese Patent Application No. 2012-225307, 3 pages, Oct. 22, 2014 (English translation only).
Seiji Takahashi, "Reasons for Submission", Third Party Submission in Japanese Patent Application No. 2012-225307, 54 pages, Oct. 22, 2014 (English translation only).
Kaketsuken, "Grounds of the Demand for Invalidation Trial," Invalidation Trial No. 2015-800162, 68 pages, received Aug. 26, 2015 (English translation only).
Kaketsuken, "Grounds of the Demand for Invalidation Trial," Invalidation Trial No. 2015-800161, 61 pages, received Aug. 26, 2015 (English translation only).
Merck & Co., Inc., "Respondent O1's Reply to Grounds of Appeal No. T0243/15-3.3.04", Opposition Against European Patent 1 868 645, 23 pages, submitted Sep. 17, 2015.
Strawman Limited, "Observations on the Grounds of Appeal", Opposition Against European Patent 1 868 645, 39 pages, submitted Sep. 17, 2015.
Zimmer, F.J., "Response to Appellant's Statement", Opposition Against European Patent No. 1 868 645, 36 pages, submitted Sep. 17, 2015.
SK Chemicals Co., Ltd, "Brief", Case No. 2015 Heo 4613 (Patent Invalidation Action), 8 pages, submitted Nov. 24, 2015 (Summarized English Translation Only).
Wyeth LLC, "Statement of Complaints Before Beijing Intellectual Property Court", Invalidation Action against Chinese Patent No. ZL 200680017776.8, 8 pages, dated Feb. 6, 2016 (English translation only).
Wyeth LLC, "Response", Invalidation Trial No. 2015-800161, 41 pages, submitted Nov. 24, 2015 (English translation only).
Henriksen, J.L., et al, "Vaccination with protein-conjugated and native type 3 capsular polysaccharide in an ethanol-fed rat model of pneumococcal pneumonia", Alcoholism:Clinical and Experimental Research 21(9):1630-1637 (1997).
Hofmann, J., et al., "The Prevalence of Drug-Resistant *Streptococcus pneumoniae* in Atlanta", New England Journal of Medicine, 333(8):481-486 (1995).
Horn, M., et al., "Safety and Immunogenicity of an Investigational 12-valent Pneumococcal Non-typeable Haemophilus influenzae Protein D Conjugate Vaccine in Toddlers: Phase I Study", 9th International Symposium on Pneumococci and Pneumococcal Diseases (Hyderabad, India), Abstract P-186 & poster (Mar. 9-13, 2014).
Huebner, R.E., et al., "Immunogenicity after one, two or three doses and impact on the antibody response to coadministered antigens of a nonavalent pneumococcal conjugate vaccine in infants of Soweto, South Africa", Pediatric Infectious Disease Journal, 21(11):1004-1007 (2002).

(56) References Cited

OTHER PUBLICATIONS

Jakobsen, H., et al., "Pneumococcal serotype 19F conjugate vaccine induces cross-protective immunity to serotype 19A in a murine pneumococcal pneumonia model", Infection and Immunity, 71(5):2956-2959 (2003).
Joloba, M.L., et al., "Pneumococcal Conjugate Vaccine Serotypes of Streptococcus pneumoniae Isolates and the Antimicrobial Susceptibility of Such Isolates in Children with Otitis Media", Clinical Infectious Diseases, 33(9):1489-1494 (2001).
Kaplan, S.L., et al., "Early Trends for Invasive Pneumococcal Infections in Children After the Introduction of the 13-valent Pneumococcal Conjugate Vaccine", The Pediatric Infectious Disease Journal, 32(3):203-207 (2013).
Kertesz, D.A., et al., "Invasive Streptococcus pneumoniae Infection in Latin American Children: Results of the Pan American Health Organization Surveillance Study", Clinical Infectious Diseases, 26(6):1355-1361 (1998).
Kieninger, D.M., et al., "Safety & Immunologic Noninferiority of 13-valent Penumococcal Conjugate Vaccine Compared to 7-valent Pneumococcal Conjugate Vaccine Given as a 4-dose Series in Healthy Infants and Toddlers", Powerpoint Presentation given at the 2nd Annual Vaccine Congres, Boston, MA (Dec. 7-9, 2008).
Kilpi, T., et al., "Protective Efficacy of a Second Pneumococcal Conjugate Vaccine against Pneumococcal Acute Otitis Media in Infants and Children: Randomized, Controlled Trial of a 7-Valent Pneumococcal Polysaccharide-Meningococcal Outer Membrane Protein Complex Conjugate Vaccine in 1666 Children", Clinical Infectious Diseases, 37:1155-1164 (2003).
Kim, L., et al., "Impact of 13-valent Pneumococcal Conjugate Vaccine (PCV13) on Invasive Pneumococcal Disease (IPD) Among Adults in the U.S.", 9th International Symposium on Pneumococci and Pneumococcal Diseases (Hyderabad, India), Abstract P-293 (Mar. 9-13, 2014).
Korean Intellectual Property Office, Chapter 2: Novelty & Chapter 4: Claims, Patent and Examination Guidelines, 13 pages, Jul. 2013 (English Translation Only).
Klein, D.L., "Pneumococcal Conjugate Vaccines: Review and Update," Microbial Drug Resistance, 1(1):49-58 (1995).
Klein, D.L., et al., "Development and testing of Streptococcus pneumoniae conjugate vaccines", Clinical Microbiology and Infection, 5(4):4S17-4S28 (1999).
Klugman, K.P., et al., A Trial of a 9-Valent Pneumococcal Conjugate Vaccine in Children with and Those without HIV InfectionNew England Journal of Medicine, 349(14):1341-1348 (2003).
Krishnamurthy, T., et al, "Characterization of the cross-reaction between type 19F(19) and 19A(57) pneumococcal capsular polysaccharides: compositional analysis and immunological relation determined with rabbit typing antisera", Infect Immun 22(3):727-735 (1978).
Lagos, R., et al., "Immunology of combining CRM197 conjugates for Streptococcus pneumoniae, Neisseria meningitis and Haemophilus influenzae in Chilean infants", Vaccine, 17(17):2299-2305 (2009).
Lange, R., et al., "Domain organization and molecular characterization of 13 two-component systems identified by genome sequencing of Streptococcus pneumoniae", Gene 237(1):223-234 (1999).
Larsen, B., et al., "Preliminary communication: the periodate-oxidation limit of alginate", Carbohyd Res 10:186-187 (1969).
Lee, C.J., et al, "Effect of culture conditions on the structure of Streptococcus pneumoniae type 19A(57) capsular polysaccharide", Infect Immun 55(8):1819-1823 (1987).
Lee, H., et al., "Immune response in infants to the heptavalent pneumococcal conjugate vaccine against vaccine-related serotypes 6A and 19A", Clinical and Vaccine Immunology, 19(3):376-381 (2009).
Lin, P.L., et al., "Incidence of Invasive Pneumococcal Disease in Children 3 to 36 Months of Age at a Tertiary Care Pediatric Center 2 Years After Licensure of the Pneumococcal Conjugate Vaccine", Pediatrics, 111(4):896-899 (2003).
Lindberg, B., et al., "Structural studies of the capsular polysaccharide from Streptococcus pneumoniae type 1", Carbohydrate Research 78(1):111-117 (1980).
Lopez, R., "Streptococcus pneumoniae and its bacteriophages: one long argument", Int Microbial 7(3):163-171 (2004).
Madore, D.V., et al., "Use of animal testing for evaluating glycoconjugate vaccine immunogenicity", Dev. Biol. Stand., 101:49-56 (1999).
Nurkka, A., et al., "Immunogenicity and Safety of the Eleven Valent Pneumococcal Polysaccharide-Protein D Conjugate Vaccine in Infants", The Pediatric Infectious Disease Journal, 23(11):1008-1014 (2004).
Martinez, A.C. et al., "Immunogenicity and Safety of 11- and 12-valent Pneumococcal Non-typeable Haemophilus influenzae Protein D-Conjugate Vaccines (11VPHID-CV, 12VPHID-CV) in Infants: Phase II Study", 9th International Symposium on Pneumococci and Pneumococcal Diseases (Hyderabad, India), Abstract P-196 & poster (Mar. 9-13, 2014).
Massaldi, H., et al., "Features of bacterial growth and polysaccharide production of Streptococcus pneumoniae serotype 14", Biotechnology and Applied Biochemistry 55(1):37-43 (2010).
Mbelle, N., et al., "Immunogenicity and Impact on Nasopharynegeal Carriage of a Nonavalent Pneumococcal Conjugate Vaccine", Journal of Infectious Disease, 180(4):1171-1176 (1999).
Merck & Co., Inc., "European Patent 1 868 645 in the name of Wyeth LLC Opposed by Merck & Co., Inc.", 11 pages, submitted Dec. 4, 2012.
Merck Sharp & Dohme Corp., PNEUMOVAX® 23 (pneumococcal vaccine polyvalent) package insert, 9 pages (2011).
Nahm, M.H., et al., "Identification of Cross-Reactive Antibodies with Low Opsonophagocytic Activity for Streptococcus pneumoniae", Journal of Infectious Disease, 176(3):698-703 (1997).
Nahm, M.H., et al., "Increase in the prevalence of the newly discovered pneumococcal serotype 6C in the nasopharynx after the introduction of pneumococcal conjugate vaccine", J. Infect. Dis., 199(3):320-325 (2009).
Nikolai, P., et al., "Vaccine adjuvants: Current state and future trends", Immunology and Cell Biology, 82:488-496 (2004).
Novartis Vaccines and Diagnostics S.R.L., "European Patent 1 868 645, Wyeth LLC, Arguments in Support of Opposition", 16 pages, submitted Dec. 7, 2012.
Nunes, M.C., et al., "Review on the immunogenicity and safety of PCV-13 in infants and toddlers," Expert Rev. Vaccines 10(7):951-980 (2011).
Obaro, S.K., et al., "Safety and immunogenicity of a nonavalent pneumococcal vaccine conjugated to CRM197 administered simultaneously but in a separate syringe with diphtheria, tetanus and pertussis vaccines in Gambian infants", Pediatr. Infect. Dis. J., 19(5):463-469 (2000).
Obaro, S.K., et al., "Safety and immunogenicity of pneumococcal conjugate vaccine in combination with diphtheria, tetanus toxoid, pertussis and Haemophilus influenzae type b conjugate vaccine", Pediatr. Infect. Dis. J., 21(10):940-946 (2002).
O'Brien, K.L., et al., "Efficacy and safety of seven-valent conjugate pneumococcal vaccine in American Indian children: group randomised trial", Lancet, 362:355-361 (2003).
O'Brien, K.L., et al., "Potential Impact of Conjugate Pneumococcal Vaccines on Pediatric Pneumococcal Diseases", American Journal of Epidemiology, 159(7):634-644 (2004).
Ohno, N., et al, "Characterization of type XIX capsular polysaccharide from Streptococcus pneumoniae IID 559", Microbiology and Immunology 26(6):523-530 (1982).
Overturf, G.D., "Pneumococcal vaccination of children", Seminars in Pediatric Infectious Diseases, 13(3):155-164 (2002).
Panacea Biotec Ltd., "Opposition of the Grant of Patent", Indian Patent Application No. 8081/DELNP/2007, 29 pages, dated Aug. 26, 2010.
Park, I.H., et al., "Discovery of a new capsular serotype (6C) within serogroup 6 of Streptococcus pneumoniae", Journal of Clinical Microbiology 45(4):1225-1233 (2007).

(56) References Cited

OTHER PUBLICATIONS

Park, I.H., et al., "Differential effects of pneumococcal vaccines against serotypes 6A and 6C", The Journal of Infectious Diseases, 198:1818-1822 (2008).
Payton, T., et al., "Safety and Tolerability of 3 Lots of 13-valent Penumococcal Conjugate Vaccine in Healthy Infants Given with Routine Pediatric Vaccinations in the USA", Poster presented at the 2nd Annual Vaccine Congress, Boston, MA (Dec. 7-9, 2008).
Penn, R.L., et al., "Antibody Responses in Adult Volunteers to Pneumococcal Polysacchride Types 19F and 19A Administered Singly and in Combination", Infection and Immunity, 1982, vol. 36(3), pp. 1261-1262.
Petrovsky, N., et al., "Vaccine adjuvants: current state and future trends", Immunology and Cell Biology 82(5):488-496 (2004).
Pfizer, Prevnar 13 (Pneumococcal 13-valent Conugate Vaccine[Diphtheria CRM197 Protein]) Package Insert, 36 pages (2011).
Porat, N., et al., "Four antibiotic-resistant *Streptococcus pneumoniae* clones unrelated to the pneumococcal conjugate vaccine serotypes, including 2 new serotypes, causing acute otitis media in Southern Israel", The Journal of Infectious Diseases, 189:385-392 (2004).
Porro, M., et al., "Immunogenic correlation between cross-reacting material (CRM197) produced by a mutant of Corynebacterium diphtheriae and diphtheria toxoid", The Journal of Infectious Diseases, 142(5):716-724 (1980).
Prymula, R., et al., "Pneumococcal capsular polysaccharides conjugated to protein D for prevention of acute otitis media caused by both *Streptococcus pneumoniae* and non-typable Haemophilus influenzae: a randomised double-blind efficacy study", Lancet, 367(9512):740-748 (2006).
Prymula, R., et al., "10-valent pneumococcal nontypeable Haemophilus influenzae PD conjugate vaccine: Synflorix", Expert Review of Vaccines, 8(11):1479-1500 (2009).
Puumalainen, T., et al., "Antibody response to an eleven valent diphtheria-and tetanus-conjugated pneumococcal conjugate vaccine in Filipino infants", The Pediatric Infectious Disease Journal, 21(4):309-314 (2002).
Puumalainen, T., et al., "Functional antibodies eleicited by an 11-valent diphtheria-tetanus toxoid-conjugated pneumococcal vaccine", The Journal of Infectious Diseases, 187:1704-1708 (2003).
Rappuoli, R., "Isolation and characterisation of Corynebacterium diphtheriae nontandem double lysogens hyperproducing CRM197", Appl. Env. Microbiol., 46(3):560-564 (1983).
Reinert, R.R., "Pneumococcal conjugate vaccines—a European perspective", International Journal of Medical Microbiology, 294:277-294 (2004).
Reinert, R.R., et al., "Pneumococcal disease caused by serotype 19A: Review of the literature and implications for future vaccine development", Vaccine 28:4249-4259 (2010).
Rennels, M.B., et al., "Safety and immunogenicity of heptavalent pneumococcal vaccine conjugated to CRM197 in United States infants", Pediatrics, 101(4):604-611 (1998).
Rennels, M., et al., Abstract for the 41st Interscience Conference on Antimicrobial Agents and Chemotherapy (ICAAC), Chicago, Ill, Sep. 22-25, 2001.
Rexroad, J., et al., "Lyophilization and the thermostability of vacciens", Cell Preservation Technology 1(2):91-104 (2002).
Robbins, J.B., et al., "Comparative immunogenicity of group 6 pneumococcal type 6A(6) and Type 6B(26) Capsular Polysaccharides", Infection and Immunity, 26(3):1116-1122 (1979).
Robbins, J.B., et al., "Considerations for Formulating the Second-Generation Pneumococcal Capsular Polysaccharide Vaccine with Emphasis on the Cross-Reactive Types", Journal of Infectious Diseases, 148:1136-1159 (1983).
Robinson, K.A., et al., "Epidemiology of Invasive *Streptococcus pneumoniae* Infections in the United States, 1995-1998", JAMA, 285(13):1729-1735 (2001).

Rudolph, K.M., et al., "Serotype Distribution and Antimicrobial Resistance Patterns of Invasive Isolates of *Streptococcus pneumoniae*: Alaska, 1991-1998", Journal of Infectious Diseases, 182(2):490-506 (2000).
Saeland, E., et al., "Serum samples from infants vaccinated with a pneumococcal conjugate vaccine, PncT, protect mice against invasive infection caused by *Streptococcus penumoniae* serotypes 6A and 6B", Journal of Infectious Diseases, 183(2):253-260 (2001).
Scott, J.E., et al., "Periodate oxidation, pKa and conformation of hexuronic acids in polyuronides and mucopolysaccharides", Biochem Biophys Acta 170:471-473 (1968).
Sigurdardottir, S. T., et al., "Safety and immunogenicity of CRM197 conjugated 9-valent pneumococcal and meningococcal C combination vaccine (9vPnCMnCC) administrated in two or three primary doses in infancy", Abstract for the 23rd Annual Meeting of the European Society for Paediatric Infectious Diseases (ESPID), Valencia, Spain, May 18-20, 2005.
Sigurdardottir, S.T., et al., "Safety and immunogenicity of CRM197-conjugated pneumococcal-meningococcal C combination vaccine (9vPnC-MnCC) whether given in two or three primary doses", Vaccine, 26(33):4178-4186 (2008).
Sigurdardottir, S. T., et al., "Two and Three Doses of the CRM197 Conjugated 9-Valent Pneumococcal and Meningococcal C Combination Vaccine (9vPnC-MnCC) in Infancy, Prime for Comparable Booster Responses at 12 Months of Age", Abstract for the 5th International Symposium on Pneumococci & Pneumococcal Diseases (ISPPD-5), Alice springs, Australia, Apr. 2-6, 2006.
SK Chemicals Co., Ltd, "Brief", Invalidation Grounds Against Korean Patent No. 1298053, 28 pages, dated Jan. 3, 2014 (English Translation only).
Skinner, J.M., et al., "Pre-clinical evaluation of a 15-valent pneumococcal conjugate vaccine (PCV15-CRM197) in an infant-rhesus monkey immunogenicity model", Vaccine, 29(48):8870-8876 (2011).
Sniadack, D.H., et al., "Potential interventions for the prevention of childhood pneumonia: geographic and temporal differences in serotype and serogroup distribution of sterile site pneumococcal isolates from children—implications for vaccine strategies", Pediatric Infectious Disease Journal, 14(6):503-510 (1995).
Strawman Limited, "Opposition Against EP-B1 1868 645", 25 pages, submitted Dec. 6, 2012.
Synflorix: European Public Assessment Report—Product Information, http://www.ema.europa.eu/docs/en_GB/document_library/EPAR_-_Product_Information/human/000973/WC500054346.pdf, accessed on Mar. 15, 2011.
Tan, T.Q., et al., "Clinical Characteristics of Children With Complicated Pneumonia Caused by *Streptococcus pneumoniae*", Pediatrics, 110(1):1-6 (2002).
Tettelin, H., et al, "Complete genome sequence of a virulent isolate of *Streptococcus pneumoniae*", Science 293(5529):498-506 (2001).
United States Patent & Trademark Office, Jan. 26, 2011, Notice of Allowance and Fee(s) Due and Notice of Allowability in U.S. Appl. No. 11/644,095.
Usonis, V., et al., "A clinical trial examining the effect of increased total CRM197 carrier protein dose on the antibody response to Haemophilus influenzae type b CRM197 conjugate vaccine", Vaccine, 26(35):4602-4607 (2008).
Vakevainen, M., et al., "Cross-Reactivity of Antibodies to Type 6B and 6A Polysaccharides of *Streptococcus pneumoniae*, Evoked by Pneumococcal Conjugate Vaccines, in Infants", Journal of Infectious Disease, 184(6):789-793 (2001).
Wessels, M.R., et al., "Structural Properties of Group B Streptococcal Type III Polysaccharide Conjugate Vaccines That Influence Immunogenicity and Efficacy", Infection & Immunity, 66(5):2186-2192 (1998).
Whitney, C.G., et al., "Increasing Prevalence of Multidrug-Resistant *Streptococcus pneumoniae* in the United States", New England Journal of Medicine, 343:1917-1924 (2000).
Whitney, C.G., et al., "Decline in Invasive Pneumococcal Disease after the Introduction of protein-Polysaccharide Conjugate Vaccine", New England Journal of Medicine, 348(18):1737-1746 (2003).

(56) References Cited

OTHER PUBLICATIONS

Wuorimaa, T., et al., "Tolerability and immunogenicity of an eleven-valent pneumococcal conjugate vaccine in healthy toddlers", The Pediatric Infectious Disease Journal, 20(3):272-277 (2001).
Wyeth, Pneumococcal 7-valent Conjugate Vaccine (Prevnar®) Package Insert, 30 pages (2009).
Wyeth LLC, "Response to First Examination Report", Indian Patent Application No. 8081/DELNP/2007, 29 pages dated Jun. 17, 2014.
Wyeth LLC, "Reply Statement of the Applicant", Indian Patent Application No. 8081/DELNP/2007, 34 pages, dated Sep. 17, 2013.
Wyeth LLC, "Patentee's Response to Notices of Opposition in European Patent No. EP1868645 (Application No. 06740419.4)", 31 pages, submitted Aug. 2, 2013.
Wyeth LLC, "Response", Case No. 2013 Dang 2673 (Invalidation Action Against Korean Patent No. 1298053), 21 pages, submitted May 7, 2014 (English Translation Only).
Wyeth LLC, "Request for Correction of Korean Patent No. 1298053", 7 pages, submitted May 7, 2014 (English Translation Only).
Xinhong, Y., et al., "Immunity to cross-reactive serotypes induced by pneumococcal conjugate vaccines in infants", The Journal of Infectious Diseases, 180:1569-1576 (1999).
Yeh, S.H., et al., "Heptavalent pneumococcal vaccine conjugated to outer membrane protein of Neisseria meningitidis serogroup b and nasopharyngeal carriage of Streptococcus pneumoniae in infants", Vaccine 21(19-21)2627-2631 (2003).
Yeh, S.H., et al., "Immunogenicity and safety of 13-valent pneumococcal conjugate vaccine in infants and toddlers", Pediatrics, 126(3):E493-E505 (2010).
Yu, X., et al., "Immunity to Cross-Reactive Serotypes Induced by Pneumococcal Conjugate Vaccines in Infants", Journal of Diseases, 180(5):1569-1576 (1999).
Zimmer, F.J., "Opposition against European Patent No. 1 868 645 (EP 06 740 419.4)", 19 pages, submitted Dec. 6, 2012.
Dagan, R., et al., "Reduction of Antibody Response to an 11-Valent Pneumococcal Vaccine Coadministered with a Vaccine Containing Acellular Pertussis Components", Infection and Immunity 72(9):5383-5391 (2004).
Declaration of Philippe Talaga, Ph.D., Opposition to European Patent No. EP1868645, 3 pages, submitted on Aug. 25, 2014.
Merck & Co., Inc., "O1's Reply to Proprietor's Submissions of Aug. 13, 2014", Opposition Against European Patent 1 868 645, 6 pages, submitted Sep. 22, 2014.
Patent Reexamination Board, "Request for Invalidation of Patent Rights", Chinese Patent No. ZL 200680017776.8, 10 pages, received Oct. 15, 2014 (English Translation Only).
Ada, G., et al, "Carbohydrate-protein conjugate vaccines", Clinical Microbiology Infection, 9(2):79-85 (2003).
Andrews, N., et al., "Effectiveness of the 13-valent pneumococcal conjugate vaccine against IPD in England and Wales", ISPPD-8, Poster No. 148 (2012).
Andrews, C.P., et al., "Safety and Immunogenicity of 15-valent Pneumococcal Conjugate Vaccine (PCV15) Compared to PCV13 in Healthy Older Adults", 9th International Symposium on Pneumococci and Pneumococcal Diseases (Hyderabad, India), Abstract O-010 & poster (Mar. 9-13, 2014).
Amdekar, Y., et al, Safety & Immunogenicity of a 13-valent Pneumococcal Conjugate Vaccine in Healthy Infants Given with Routine Vaccines in India:; Abstract submitted Dec. 2008—7th Intl. Symposium on Antimicrobial Agents and Resistance, Bangkok, Thailand, (Mar. 18-20, 2009).
Anderson, P., et al., "Immunization of 2-month-old infants with protein-coupled oligosaccharides derived from the capsule of Haemophilus influenzae type b", Journal of Pediatrics, 107(3):346-351 (1985).
Anderson, P., et al., "Non-interference between two protein carriers when used with the same polysaccharide for pneumococcal conjugate vaccines in 2-year-old children", Vaccine 21:1554-1559 (2003).

Benaissa-Trouw, B., et al., "Synthetic polysaccharide type 3-related di-, tri-, and tetrasaccharide-CRM197 conjugates induce protection against Streptococcus pneumoniae type 3 in mice", Infection and Immunity 69(7):4698-4701 (2001).
Black, S., et al., "Safety and efficacy of the seven-valent pneumococcal conjugate vaccine: evidence from Northern California", Eur J Pediatr 161:S127-S131 (2002).
Black, S., et al., "Efficacy, safety and immunogenicity of heptavalent pneumococcal conjugate vaccine in children", Pediatric Infectious Disease Journal, 19(3):187-195 (2000).
Black, S., et al., "Postlicensure evaluation of the effectiveness of seven valent pneumococcal conjugate vaccine", Pediatric Infectious Disease Journal, 20(12):1105-1107 (2001).
Block, S.L., e al., "Pneumococcal serotypes from acute otitis media in rural Kentucky", Pediatric Infectious Disease Journal, 21(9):859-865 (2002).
Bonten, M., et al., "Community Acquired Pneumonia Immunisation Trial in Adults (CAPITA)", 9th International Symposium on Pneumococci and Pneumococcal Diseases (Hyderabad, India), Abstract O-015 (Mar. 9-13, 2014).
Brito, D.A., et al., "Serotyping Streptococcus pneumoniae by multiplex PCR", Journal of Clinical Microbiology, 41(6):2378-2384 (2003).
Buckingham, S.C., et al., "Incidence and etiologies of complicated parapneumonic effusions in children, 1996 to 2001", Pediatric Infectious Disease Journal, 22:499-504 (2003).
Butler, J.C., et al., "Serotype Distribution of Streptococcus pneumoniae Infections among Preschool Children in the United States, 1978-1994: Implications for Development of a Conjugate Vaccine", Journal of Infectious Diseases, 171(4):885-889 (1995).
Buttery, J.P., et al., Immunogenicity and Safety of a Combination Pneumococcal-Meningococcal Vaccine in Infants: A Randomized Controlled Trial JAMA, 293(14):1751-1758 (2005).
Byington, C.L., et al., An Epidemiological Investigation of a Sustained High Rate of Pediatric Parapneumonic Empyema: Risk Factors and Microbiological Associations CarrieClinical Infectious Diseases, 34(4):434-440 (2002).
Choo, S., et al., "Immunogenicity and reactogenicity of a pneumococcal conjugate vaccine administered combined with a Haemophilus influenzae type b conjugate vaccine in United Kingdom infants", Pediatric Infectious Diseases Journal, 19(9):854-862 (2000).
Committee on Infectious Diseases, "Policy Statement: Recommendations for the Prevention of Pneumococcal Infections, Including the Use of Pneumococcal Conjugate Vaccine (Prevnar), Pneumococcal Polysaccharide Vaccine, and Antibiotic Prophylaxis", Pediatrics, 106(2):362-366 (2000).
Cooper, D., et al., "The 13-valent pneumococcal conjugate vaccine (PCV13) elicits cross-functional opsonophagocytic killing responses in humans to Streptococcus pneumoniae serotypes 6C and 7A", Vaccine, 29:7207-7211 (2011).
Cripps, A.W., et al., "Bacterial otitis media: a vaccine preventable disease?", Vaccine, 23:2304-2310 (2005).
Crucell Holland B.V., "Opposition by Crucell Holland B.V. Against the Grant of EP 1 868 645 B1 in the name of Wyeth LLC", 18 pages, submitted Dec. 7, 2012.
Cutts, F., et al., "Efficacy of nine-valent pneumococcal conjugate vaccine against pneumonia and invasive pneumococcal disease in The Gambia: randomised, double-bind, placebo-controlled trial", Lancet, 365:1139-1146 (2005).
Dagan, R., et al., "Effect of a conjugate pneumococcal vaccine on the occurrence of respiratory infections and antibiotic use in daycare center attendees", The Pediatric Infectious Disease Journal, 20(10):951-958 (2001).
Dagan, R., et al., "Reduction of Nasopharyngeal Carriage of Streptococcus pneumoniae after Administration of a 9-Valent Pneumococcal Conjugate Vaccine to Toddlers Attending Day Care Centers", Journal of Infectious Diseases, 185:927-936 (2002).
Dagan, R., et al., "Effect of a nonavalent conjugate vaccine on carriage of antibiotic-resistant Streptococcus pneumoniae in day-care centers", Pediatr. Infect. Dis. J., 22(6):532-539 (2003).
Dagan, R., et al., "Glycoconjugate vaccines and immune interference: A review", Vaccine, 28:5513-5523 (2010).

(56) References Cited

OTHER PUBLICATIONS

Dagan, R. et al., "Reduced Response to Multiple Vaccines Sharing Common Protein Epitopes that are Administered Simultaneously to Infants", Infection and Immunity 66(5):2093-2098 (1998).
Daum, R.S., et al. "Infant immunization with pneumococcal CRM197 vaccines: effect of saccharide size on immunogenicity and interactions with simultaneously administered vaccines", J Infect Dis 176:445-455 (1997).
De La Pena, C., et al., "Present and future of the vaccination against pneumonia", Pediatrika, 24(4):147-155 (2004).
Declaration of Gregg C. Sylvester, MD, MPH, Opposition to European Patent No. EP1868645, 3 pages, submitted on Aug. 2, 2013 (unsigned).
Declaration of Peter Paradiso, Ph.D., Opposition to European Patent No. EP1868645, 5 pages, submitted on Aug. 2, 2013.
Dudley, S., et al., "Bacterial pathogens of otitis media and sinusitis: Detection in the nasopharynx with selective agar media", The Journal of Laboratory and Clinical Medicine, 138(5):338-342 (2001).
Eltringham, G., et al., "Culture-Negative Childhood Empyema Is Usually Due to Penicillin-Sensitive *Streptococcus pneumoniae* Capsular Serotype 1", Journal of Clinical Microbiology, 41(1):521-522 (2003).
EMEA, Public Statement: Prevenar—Shortage of Supply, 2 pages, Mar. 22, 2004, available at http://www.ema.europa.eu/docs/en_GB/document_library/Public_statement/2009/12/WC500017611.pdf.
Eskola, J., et al., "Efficacy of a Pneumococcal Conjugate Vaccine against Acute Otitis Media", New England Journal of Medicine, 344(6):403-409 (2001).
European Patent Office, "Summons to Attend Oral Proceedings", Opposition to European Patent No. EP1868645, 13 pages, dated Jan. 31, 2014.
EU Clinical Trials Register, EudraCT No. 2011-005743-27, 16 pages, available at https://www.clinicaltrialsregister.eu/ctr-search/trial/2011-005743-27/DE (accessed on Jul. 29, 2013).
Fagan R.L., et al., "The epidemiology of invasive pneumococcal disease in children in Far North Queensland", Journal of Paediatrics and Child Health, 37(6):571-575 (2001).
Fattom, A., et al., "Epitopic overload at the site of injection may result in suppression of the immune response to combined capsular polysaccharide conjugate vaccines", Vaccine, 17(2):126-133 (1999).
Foster, D., et al., "Invasive pneumococcal disease: epidemiology in children and adults prior to implementation of the conjugate vaccine in the Oxfordshire region, England", Journal of Medical Microbiology 57(4):480-487 (2008).
Gatchalian. S.R., et al, 17th Annual Meeting of the Eur. Soc. Paed. Infe. Dis. (ESPID), Poster No. 4, P1A poster Session 1, Istanbul, Turkey (Mar. 27, 2001).
Giebink, G.S., et al., "Immunogenicity and Efficacy of *Streptococcus pneumoniae* Polysaccharide-Protein Conjugate Vaccines against Homologous and Heterologous Serotypes in the Chinchilla Otitis Media Model", Journal of Infectious Diseases, 173(1):119-127 (1996).
Greenberg, D., et al., "Safety and Immunogenicity of 15-valent Pneumococcal Conjugate Vaccine (PCV-15) Compared to PCV-13 in Healthy Infants" [Abstract ISPPD-0197], Pneumonia, 3:99 (2014).
Hausdorff, W.P., et al., "Which Pneumococcal Serogroups Cause the Most Invasive Disease: Implications for Conjugate Vaccine Formulation and Use, Part 1", Clinical Infectious Diseases, 30(1):100-121 (2000).
Hausdorff, W.P., et al., "The Contribution of Specific Pneumococcal Serogroups to Different Disease Manifestations: Implications for Conjugate Vaccine Formulation and Use, Part II", Clinical Infectious Diseases, 30(1):122-140 (2000).
Hausdorff, W.P., et al., "Invasive pneumococcal disease in children: geographic and temporal variations in incidence and serotype distribution", European Journal of Pediatrics, 161(Suppl. 2):S135-139 (2002).
Hausdorff, W.P., et al., "Epidemiological differences among pneumococcal serotypes", Lancet Infectious Diseases, 5(2):83-93 (2005).
Hausdorff, W.P., et al., "Geographical differences in invasive pneumococcal disease rates and serotype frequency in young children", Lancet, 357(9260):950-952 (2001).
Hausdorff, W.P., et al., "Multinational study of pneumococcal serotypes causing acute otitis media in children", Pediatric Infectious Disease Journal, 21(11):1008-1016 (2002).
European Patent Office, "Decision Revoking the European Patent", Opposition to European Patent No. EP1868645, 36 pages, dated Dec. 22, 2014.
Intellectual Property Tribunal, "Decision", Case No. 2013 Dang 2673 (Invalidation Action Against Korean Patent No. 1298053), 28 pages, dated Jun. 10, 2015 (English Translation only).
Moore, M.R., "Update on effectiveness and impact of PCV13 use among U.S. children", Centers for Disease Control & Prevention Presentation, 13 pages (Feb. 26, 2014).
SK Chemicals Co., Ltd, "Brief", Case No. 2013 Dang 2673 (Patent Invalidation Action against KR 1298053), 19 pages, dated Jan. 20, 2015 (English Translation only).
SK Chemicals Co., Ltd, "Technical Presentation", Case No. 2013 Dang 2673 (Patent Invalidation Action against KR 1298053), 41 pages, dated Jan. 22, 2015 (English Translation only).
SK Chemicals Co., Ltd, "Brief", Case No. 2013 Dang 2673 (Patent Invalidation Action against KR 1298053), 32 pages, dated Mar. 2, 2015 (English Translation only).
SK Chemicals Co., Ltd, "Brief I", Case No. 2015 Heo 4613 (Patent Invalidation Action against KR 1298053), 28 pages, dated Sep. 3, 2015 (English Translation only).
SK Chemicals Co., Ltd, "Brief II", Case No. 2015 Heo 4613 (Patent Invalidation Action against KR 1298053), 4 pages, dated Sep. 2015 (Summarized English Translation only).
Wyeth LLC, "Brief", Case No. 2013 Dang 2673 (Invalidation Action Against Korean Patent No. 1298053), 14 pages, submitted Jan. 9, 2015 (English Translation Only).
Wyeth LLC, "Technical Presentation", Case No. 2013 Dang 2673 (Invalidation Action Against Korean Patent No. 1298053), 60 pages, Jan. 22, 2015 (English Translation Only).
Wyeth LLC, "Brief", Case No. 2013 Dang 2673 (Invalidation Action Against Korean Patent No. 1298053), 13 pages, submitted Mar. 2, 2015 (English Translation Only).
Wyeth LLC, "Brief", Case No. 2013 Dang 2673 (Invalidation Action Against Korean Patent No. 1298053), 15 pages, submitted Mar. 16, 2015 (English Translation Only).
Wyeth LLC, "Brief", Case No. 2013 Dang 2673 (Invalidation Action Against Korean Patent No. 1298053), 23 pages, submitted Apr. 27, 2015 (English Translation Only).
Wyeth LLC, "Brief", Case No. 2013 Dang 2673 (Invalidation Action Against Korean Patent No. 1298053), 14 pages, submitted May 7, 2015 (English Translation Only).
Wyeth LLC, "Grounds of Appeal in Accordance to Article 108 and Rule 99(2) EPC", Opposition Against European Patent No. EP1868645, 33 pages submitted on May 4, 2015.

* cited by examiner

PROCESS FOR PREPARING PNEUMOCOCCAL POLYSACCHARIDE-PROTEIN CONJUGATES

CROSS REFERENCE TO RELATED APPLICATIONS

This is a Continuation of U.S. application Ser. No. 14/322,057, filed Jul. 2, 2014, which is a Continuation of U.S. application Ser. No. 13/439,111, filed Apr. 4, 2012, now issued as U.S. Pat. No. 8,808,708, which is a Continuation of U.S. application Ser. No. 12/357,853, filed Jan. 22, 2009, now issued as U.S. Pat. No. 8,895,024, which is a Continuation of U.S. application Ser. No. 11/395,593, filed Mar. 31, 2006, now abandoned, which claims priority to U.S. Provisional Patent Application 60/669,605, filed Apr. 8, 2005, the contents of which are herein incorporated by reference in their entirety.

FIELD OF THE INVENTION

The present invention relates generally to the field of medicine, and specifically to microbiology, immunology, vaccines and the prevention of infection by a bacterial pathogen by immunization.

BACKGROUND OF THE INVENTION

*Streptococcus pneumoniae* is a leading cause of meningitis, pneumonia, and severe invasive disease in infants and young children throughout the world. The multivalent pneumococcal polysaccharide vaccines have been licensed for many years and have proved valuable in preventing pneumococcal disease in elderly adults and high-risk patients. However, infants and young children respond poorly to most pneumococcal polysaccharides. The 7-valent pneumococcal conjugate vaccine (7vPnC, PREVNAR®) was the first of its kind demonstrated to be highly immunogenic and effective against invasive disease and otitis media in infants and young children. This vaccine is now approved in many countries around the world. PREVNAR® (7vPnC) contains the capsular polysaccharides from serotypes 4, 6B, 9V, 14, 18C, 19F and 23F, each conjugated to a carrier protein designated $CRM_{197}$. PREVNAR® (7vPnC) covers approximately 80-90%, 60-80%, and 40-80% of invasive pneumococcal disease (IPD) in the US, Europe, and other regions of the world, respectively [1, 2]. Surveillance data gathered in the years following the introduction of PREVNAR® (7vPnC) has clearly demonstrated a reduction of invasive pneumococcal disease in US infants as expected (FIG. 1) [3,4].

Surveillance of IPD conducted in US infants prior to the introduction of PREVNAR® (7vPnC) demonstrated that a significant portion of disease due to serogroups 6 and 19 was due to the 6A (approximately one-third) and 19A (approximately one-fourth) serotypes [5,6]. Pneumococcal invasive disease surveillance conducted in the US after licensure of PREVNAR® (7vPnC) suggests that a large burden of disease is still attributable to serotypes 6A and 19A (FIG. 1) [3]. Moreover, these two serotypes account for more cases of invasive disease than serotypes 1, 3, 5, and 7F combined (8.2 vs. 3.3 cases/100,000 children 2 years and under). In addition, serotypes 6A and 19A are associated with high rates of antibiotic resistance (FIG. 2) [7, 8, 9]. While it is possible that serogroup cross-protection will result in a decline of serotype 6A and 19A disease as more children are immunized, there is evidence to suggest that there will be a limit to the decline, and a significant burden of disease due to these serotypes will remain (see below).

Given the relative burden and importance of invasive pneumococcal disease due to serotypes 1, 3, 5, 6A, 7F, and 19A, adding these serotypes to the PREVNAR® (7vPnC) formulation would increase coverage for invasive disease to >90% in the US and Europe, and as high as 70%-80% in Asia and Latin America. This vaccine would significantly expand coverage beyond that of PREVNAR® (7vPnC), and provide coverage for 6A and 19A that is not dependent on the limitations of serogroup cross-protection.

SUMMARY OF THE INVENTION

Accordingly, the present invention provides generally a multivalent immunogenic composition comprising 13 distinct polysaccharide-protein conjugates, wherein each of the conjugates contains a capsular polysaccharide from a different serotype of *Streptococcus pneumoniae* conjugated to a carrier protein, together with a physiologically acceptable vehicle. Optionally, an adjuvant, such as an aluminum-based adjuvant, is included in the formulation. More specifically, the present invention provides a 13-valent pneumococcal conjugate (13vPnC) composition comprising the seven serotypes in the 7vPnC vaccine (4, 6B, 9V, 14, 18C, 19F and 23F) plus six additional serotypes (1, 3, 5, 6A, 7F and 19A).

The present invention also provides a multivalent immunogenic composition, wherein the capsular polysaccharides are from serotypes 1, 3, 4, 5, 6A, 6B, 7F, 9V, 14, 18C, 19A, 19F and 23F of *Streptococcus pneumoniae* and the carrier protein is $CRM_{197}$.

The present invention further provides a multivalent immunogenic composition, wherein the capsular polysaccharides are from serotypes 1, 3, 4, 5, 6A, 6B, 7F, 9v, 14, 18C, 19A, 19F and 23F of *Streptococcus pneumoniae*, the carrier protein is $CRM_{197}$, and the adjuvant is an aluminum-based adjuvant, such as aluminum phosphate, aluminum sulfate and aluminum hydroxide. In a particular embodiment of the invention, the adjuvant is aluminum phosphate.

The present invention also provides a multivalent immunogenic composition, comprising polysaccharide-protein conjugates together with a physiologically acceptable vehicle, wherein each of the conjugates comprises a capsular polysaccharide from a different serotype of *Streptococcus pneumoniae* conjugated to a carrier protein, and the capsular polysaccharides are prepared from serotype 3 and at least one additional serotype.

In one embodiment of this multivalent immunogenic composition, the additional serotype is selected from the group consisting of serotypes 1, 4, 5, 6A, 6B, 7F, 9V, 14, 18C, 19A, 19F, and 23F. In another embodiment, the carrier protein is $CRM_{197}$. In yet another embodiment, the composition comprises an adjuvant, such as an aluminum-based adjuvant selected from aluminum phosphate, aluminum sulfate and aluminum hydroxide. In a particular embodiment, the adjuvant is aluminum phosphate.

The present invention also provides a multivalent immunogenic composition, comprising polysaccharide-protein conjugates together with a physiologically acceptable vehicle, wherein each of the conjugates comprises a capsular polysaccharide from a different serotype of *Streptococcus pneumoniae* conjugated to a carrier protein, and the capsular polysaccharides are prepared from serotypes 4, 6B, 9V, 14, 18C, 19F, 23F and at least one additional serotype.

In one embodiment of this multivalent immunogenic composition, the additional serotype is selected from the group consisting of serotypes 1, 3, 5, 6A, 7F, and 19A. In another embodiment, the carrier protein is $CRM_{197}$. In yet another embodiment, the composition comprises an adjuvant, such as an aluminum-based adjuvant selected from aluminum phosphate, aluminum sulfate and aluminum hydroxide. In a particular embodiment, the adjuvant is aluminum phosphate.

The present invention also provides a method of inducing an immune response to a *Streptococcus pneumoniae* capsular polysaccharide conjugate, comprising administering to a human an immunologically effective amount of any of the immunogenic compositions just described.

The present invention further provides that any of the immunogenic compositions administered is a single 0.5 mL dose formulated to contain: 2 μg of each saccharide, except for 6B at 4 μg; approximately 29 μg $CRM_{197}$ carrier protein; 0.125 mg of elemental aluminum (0.5 mg aluminum phosphate) adjuvant; and sodium chloride and sodium succinate buffer as excipients.

DETAILED DESCRIPTION OF THE INVENTION

Figure 1:
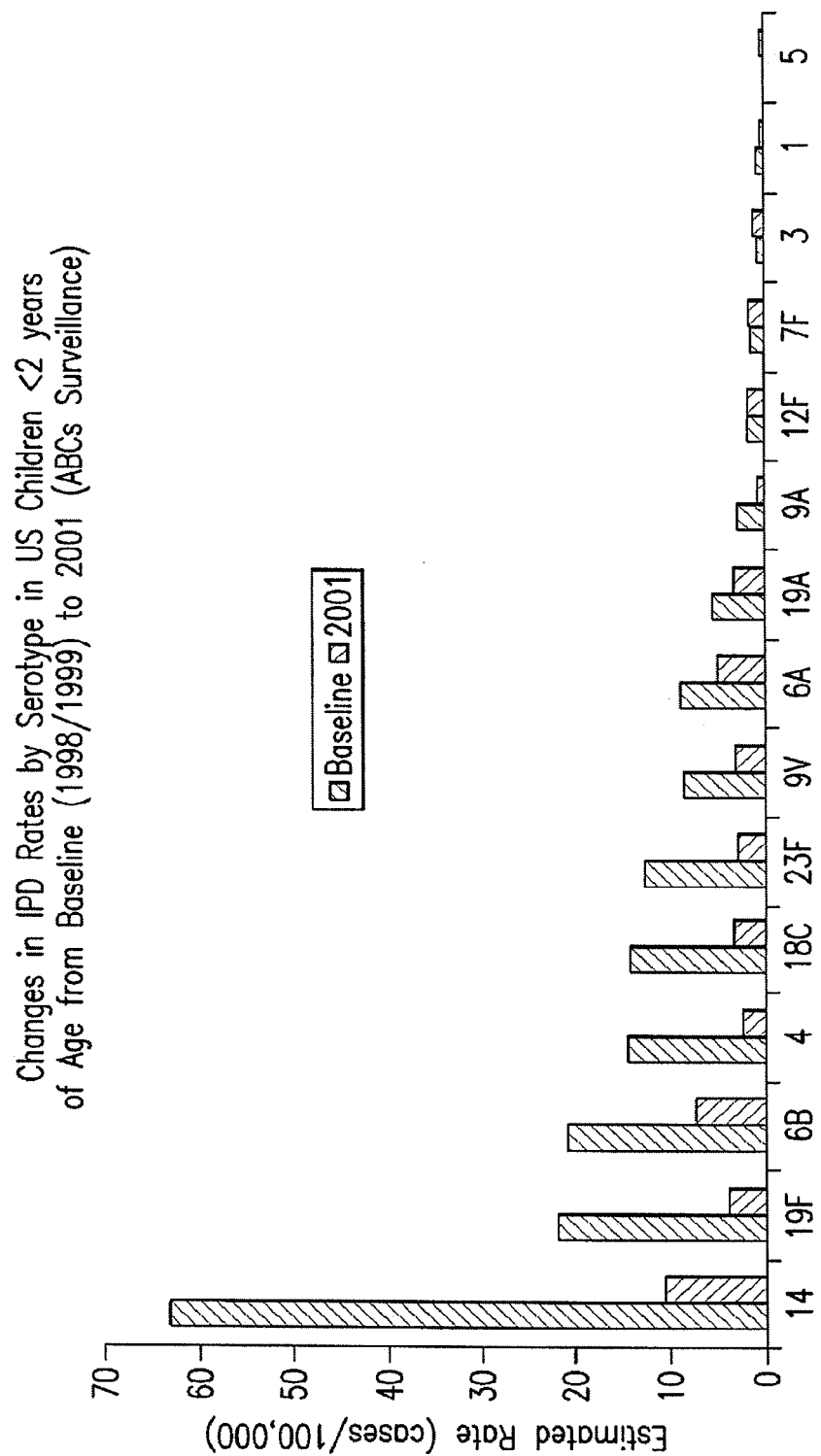
FIG. 1 depicts the changes in IPD rates by serotype in US children <2 years of age from baseline (1998/1999) to 2001.

Inclusion of PREVNAR® (7vPnC) Serotypes 4, 6B, 9V, 14, 18C, 19F, 23F

Data from IPD surveillance between 1995-1998 estimated that the seven serotypes in PREVNAR® (7vPnC) were responsible for around 82% of IPD in children <2 years of age [5]. In Northern California, the site of the efficacy trial, the PREVNAR® (7vPnC) serotypes accounted for 90% of all cases of IPD in infants and young children [10]. Since introduction of the PREVNAR® (7vPnC) vaccine in 2000, there has been a significant decrease in the overall IPD rates due to a decrease in disease due to the vaccine serotypes [3, 4]. Therefore, there is no justification at this time to remove any of the PREVNAR® (7vPnC) serotypes from the next generation of pneumococcal conjugate vaccines but rather to add serotypes to obtain wider coverage.

Inclusion of Serotypes 1, 3, 5 and 7F

In the US, the rate of IPD caused by serotype 1 in children under the age of 5 years is <2%, about the same as for each of types 3 and 7F [1, 6]. Serotypes 1 and 5 account for higher rates of IPD in US populations at high risk for invasive pneumococcal disease. Specifically, serotype 1 causes 3.5% of IPD in Alaskan native children <2 years of age, and 18% in children 2-4 years of age [11]. Both serotype 1 and serotype 5 significantly cause disease in other parts of the world and in indigenous populations in developed countries [12, 13, 14].

Serotype 1 may also be associated with more severe disease as compared with other pneumococcal serotypes [15]. This observation is based on the difference in rates of case identification between the US and Europe, and the associated difference in medical practice. Overall, the incidence of IPD is lower in Europe than in the US. However, the percent of IPD caused by serotype 1 in Europe is disproportionately higher than in the US (6-7%, vs. 1-2%, respectively). In Europe, blood cultures are obtained predominantly from hospitalized children. In the US, it is routine medical practice to obtain blood cultures in an outpatient setting from children presenting with fever ≥39° C. and elevated white blood cell counts. Given the difference in medical practice, it is postulated that the lower percent of disease caused by serotype 1 in the US may be diluted by higher rates of other serotypes causing milder disease, while the higher percent in Europe reflects more serious disease. In addition, seroepidemiology studies of children with complicated pneumonia demonstrate that serotype 1 is disproportionately represented [16, 17, 18]. This suggests that inclusion of serotype 1 may reduce the amount of severe pneumococcal disease, as well as, contribute to a total reduction in invasive pneumococcal disease.

The addition of serotypes 3 and 7F will increase coverage against IPD in most areas of the world by approximately 3%-7%, and in Asia by around 9%. Thus, an 11-valent vaccine would cover 50% in Asia and around 80% of IPD in all other regions [1, 2]. These serotypes are also important with respect to otitis media coverage [19]. In a multinational study of pneumococcal serotypes causing otitis media, Hausdorff et al found serotype 3 to be the 8th most common middle ear fluid isolate overall [20]. Serotype 3 accounted for up to 8.7% of pneumococcal serotypes associated with otitis media. Thus, the importance of types 3 and 7F in otitis media, as well as in IPD, warrants their inclusion in a pneumococcal conjugate vaccine.

However, attempts to produce a multivalent pneumococcal conjugate vaccine that exhibits significant immunogenicity with respect to serotype 3 polysaccharides have been unsuccessful. For example, in a study of the immunogenicity and safety of an 11-valent pneumococcal protein D conjugate vaccine (11-Pn-PD), no priming effect was observed for serotype 3 in infants who had received three doses of the vaccine followed by a booster dose of either the same vaccine or a pneumococcal polysaccharide vaccine (Nurkka et al. (2004) *Ped. Inf. Dis. J.*, 23:1008-1014). In another study, opsonophagocytic assay (OPA) results from infants who had received doses of 11-Pn-PD failed to show antibody responses for serotype 3 at levels comparable to other tested serotypes (Gatchalian et al., 17th Annual Meeting of the Eur. Soc. Paed. Inf. Dis. (ESPID), Poster No. 4, P1A Poster Session 1, Istanbul Turkey, Mar. 27, 2001). In yet another study, which assessed the efficacy of an 11-Pn-PD in the prevention of acute otitis media, the vaccine did not provide protection against episodes caused by serotype 3 (Prymula et al. www.thelancet.com, Vol. 367: 740-748 (Mar. 4, 2006)). Accordingly, a pneumococcal conjugate vaccine comprising capsular polysaccharides from serotype 3 and capable of eliciting an immunogenic response to serotype 3 polysaccharides provides a significant improvement over the existing state of the art.

Inclusion of Serotypes 6A and 19A a. Epidemiology of Serotypes 6A and 19A

Surveillance data in the literature suggest that serotypes 6A and 19A account for more invasive pneumococcal disease in US children <2 years of age than serotypes 1, 3, 5, and 7F combined (FIG. 1) [1,5]. In addition, these serotypes are commonly associated with antibiotic resistance (FIG. 2) and play an important role in otitis media [6, 19, 20]. The ability of the current PREVNAR® (7vPnC) vaccine to protect against disease due to 6A and 19A is not clear. The rationale for inclusion of 6A and 19A components in a 13vPnC vaccine is discussed below.

b. Responses to 6A and 19A Induced by 6B and 19F Polysaccharides

The licensed unconjugated pneumococcal polysaccharide vaccines (for use in persons at least two years of age) have contained 6A or 6B capsular polysaccharide but not both [21]. Immunogenicity data generated at the time of formulation of the 23-valent pneumococcal polysaccharide vaccine demonstrated that a 6B monovalent vaccine induced antibody to both the 6A and 6B capsules. The data from several trials assessing IgG and opsonophagocytic assay (OPA) responses in a variety of populations with free polysaccharide and with pneumococcal conjugate vaccines suggested that IgG responses to 6A are induced by 6B antigens, but the responses are generally lower, and the OPA activity with 6A organisms is different than with 6B organisms [22,23,24,25]. In addition, subjects responding with high 6B antibody may have little or no activity against 6A.

In contrast to the chemical composition of the 6A and 6B capsular polysaccharides where there exists a high degree of similarity, the 19A and 19F capsules are quite different due to the presence of two additional side chains in the 19A polysaccharide. Not surprisingly, immune responses measured in human volunteers immunized with 19F polysaccharide vaccine showed that responses to 19F were induced in 80% of subjects, but only 20% of subjects had a response to 19A [26]. Low levels of cross-reactive IgG and OPA responses to serotype 19A after immunization with 19F polysaccharide have also been documented in trials with conjugate vaccines as well [24,26].

Figure 3:
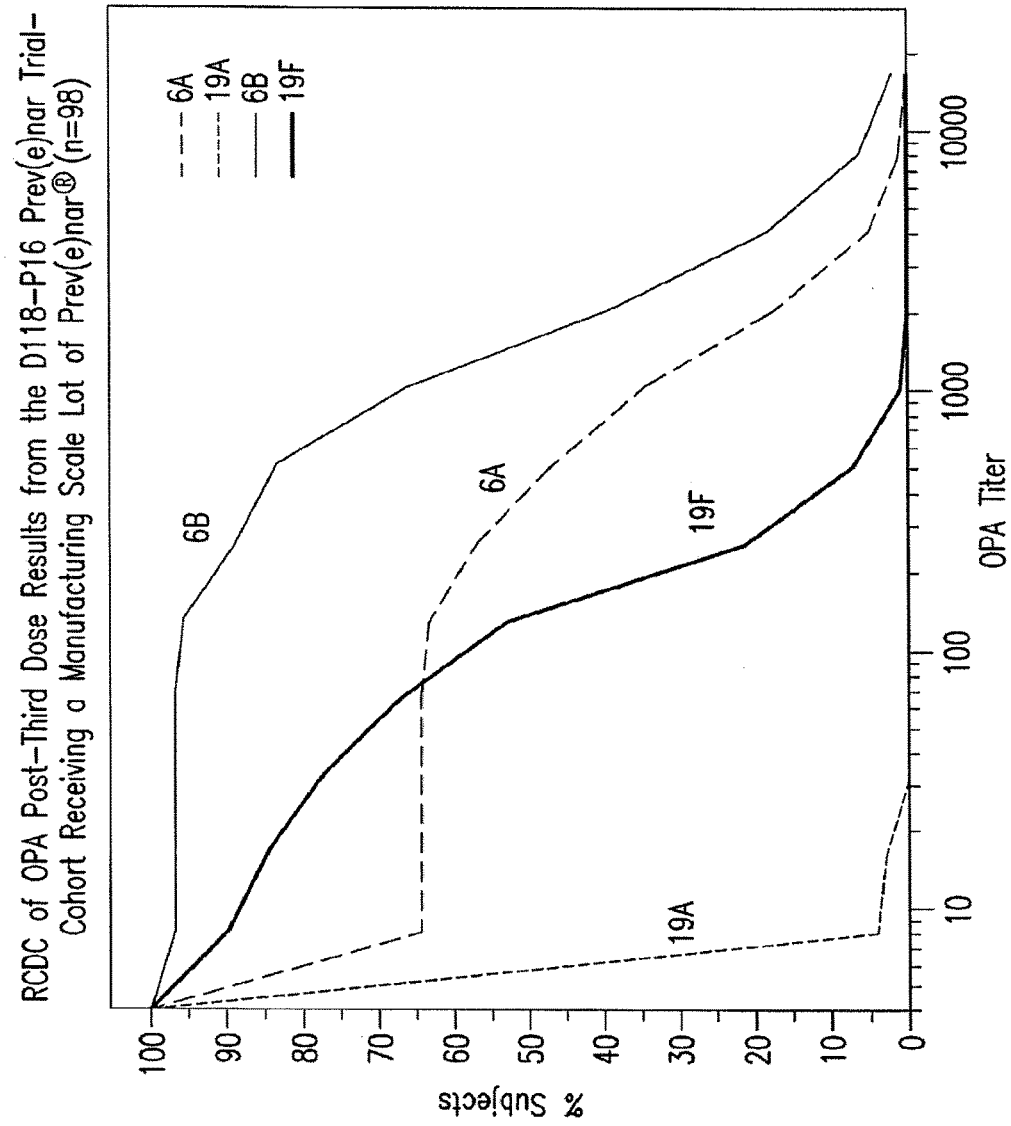
FIG. 3 depicts the reverse cumulative distribution curves (RCDC) of OPA post-third dose results from the D118-P16 PREVNAR® (7vPnC) trial.

Internal data on cross-reactive OPA responses to 6A and 19A have been generated from the 7vPnC bridging trial (D118-P16) conducted in US infants (FIG. 3). These studies are consistent with the findings of others, and demonstrate induction of cross-reactive functional antibody to 6A polysaccharide after immunization with 6B polysaccharide, although at a lower level, and very little functional antibody to 19A after immunization with 19F.

Impact of 6B and 19F Immunization on 6A and 19A in Animal Models

Animal models have been used to evaluate the potential for cross-protection with polysaccharide immunization. In an otitis media model developed by Giebink et al., chinchillas were immunized with a tetravalent polysaccharide outer membrane protein (OMP) conjugate vaccine (containing 6B, 14, 19F, 23F saccharides) or placebo [27]. In this trial there appeared to be some cross-protection for 6A; however this did not reach statistical significance and the level of protection was lower than with 6B against otitis media. In this same model there was 100% protection against 19F otitis media, but only 17% protection against 19A otitis media.

Saeland et al. used sera from infants immunized with an 8-valent pneumococcal tetanus conjugate vaccine (containing 6B and 19F) to passively immunize mice prior to an intranasal challenge with 6A organisms, in a lung infection model [28]. Of the 59 serum samples, 53% protected mice against bacteremia with 6B and 37% protected against 6A. Mice passively immunized with sera from infants immunized with four doses of an 11-valent pneumococcal conjugate vaccine (containing 19F conjugated to tetanus toxoid) were given an intranasal challenge with 19A organisms in the same model [29]. Of 100 mice passively immunized and then challenged, 60 mice had no 19A organisms detected in lung tissue, whereas organisms were identified in all mice given saline placebo. However, passive immunization did not protect against challenge with 19F organisms in this model; therefore, the relevance of the model for serogroup 19 is questionable. In general these models provide evidence of some biological impact of 6B immunization on 6A organisms although the effect on the heterologous serotype was not as great as that observed with the homologous serotype. The impact of 19F immunization on 19A organisms is not well understood from these models.

Impact of 6B and 19F Polysaccharide Conjugate Immunization on 6A and 19A Disease in Efficacy/Effectiveness Trials The number of cases of disease due to the 6B, 6A, 19F and 19A serotypes in 7vPnC and 9vPnC (7vPnC plus serotypes 1 and 5) efficacy trials is noted in Table 1 [30, 10, 31]. The numbers of invasive disease cases are too small to allow any conclusions to be drawn for serotypes 6A and 19A. However, the Finnish otitis media trial generated a large number of pneumococcal isolates [32]. In the per protocol analysis 7vPnC was 84% (95% CI 62%, 93%) efficacious against otitis media due to serotype 6B and 57% (95% CI 24%, 76%) efficacious against otitis media due to serotype 6A (Table 1). In contrast, serotype-specific efficacy with the 7vPnC was not demonstrated for otitis media due to either 19F or 19A.

TABLE 1

Cases of Pneumococcal Disease Due to Serotypes 6B, 6A, 19F, and 19A in Efficacy Trials with the 7vPnC and 9vPnC Vaccines

| | 6B | | 6A | | 19F | | 19A | |
|---|---|---|---|---|---|---|---|---|
| | PnC | Contr. | PnC | Contr. | PnC | Contr. | PnC | Contr. |
| Kaiser Efficacy Trial - 7vPnC (ITT) | 1 | 7 | 0 | 1 | 2* | 13 | 0 | 1 |
| Navajo Efficacy Trial - 7vPnC (ITT) | 0 | 5 | 1 | 0 | 1 | 1 | 1 | 0 |
| South African Efficacy Trial - 9vPnC HIV (−) (ITT) | 1 | 2 | 1 | 0 | 0 | 1 | 3 | 1 |
| South African Efficacy Trial - 9vPnC HIV (+) (ITT) | 1 | 7 | 3 | 10 | 2 | 3 | 2 | 3 |

TABLE 1-continued

Cases of Pneumococcal Disease Due to Serotypes 6B, 6A, 19F,
and 19A in Efficacy Trials with the 7vPnC and 9vPnC Vaccines

|  | 6B | | 6A | | 19F | | 19A | |
| --- | --- | --- | --- | --- | --- | --- | --- | --- |
|  | PnC | Contr. | PnC | Contr. | PnC | Contr. | PnC | Contr. |
| Finnish Otitis Media Trial - 7vPnC (PP) | 9* | 56 | 19* | 45 | 43 | 58 | 17 | 26 |

*Statistically significant efficacy demonstrated From references 30, 10 and 33, and personal communications
Contr = control
ITT = intention to treat analysis
PP = per protocol analysis Post-marketing IPD surveillance data is also available from a case-control trial conducted by the Centers for Disease Control to evaluate the effectiveness of PREVNAR® (7vPnC) [33]. Cases of pneumococcal invasive disease occurring in children 3 to 23 months of age were identified in the surveillance laboratories and matched with three control cases by age and zip code. After obtaining consent, medical and immunization history (subjects were considered immunized if they had received at least one dose of PREVNAR® (7vPnC)) was obtained from parents and medical providers for cases and controls. The preliminary results were presented at the 2003 ICAAC meeting and a summary of the findings for 6B, 19F, 19A and 6A disease is presented in Table 2. These data indicate that PREVNAR® (7vPnC) is able to prevent disease due to 6A, although at a level that may be somewhat lower than serotype 6B disease. These data also indicate that the cross-protection for invasive disease due to 19A is limited.

TABLE 2

Preliminary results of a Case Control Trial Performed by the CDC (presented at ICAAC, 2003)

| Serotype | Informative Sets, n | VE* (95% CI) |
| --- | --- | --- |
| Vaccine Type, All | 115 | 94 (87, 97) |
| Vaccine Related, All | 36 | 70 (38, 86) |
| Non-Vaccine Type, All | 43 | -4 (-106, 48) |
| 6B | 27 | 94 (72, 99) |
| 19F | 19 | 73 (16, 92) |
| 6A | 15 | 87 (53, 97) |
| 19A | 16 | 40 (-87, 80) |

*Vaccine effectiveness comparing vaccinated (≥1 dose) vs. unvaccinated, and adjusted for underlying conditions Reference 40 and personal/confidential communication A published analysis [3] of the use of PREVNAR® (7vPnC) also indicated that serotypes 6B and 19F conferred a moderate reduction in IPD caused by serotypes 6A and 19A among children under two years of age (Table 1 in [3]). Disease rates among unimmunized adults caused by serotypes 6A, 9A, 9L, 9N, 18A, 18B, 18F, 19A, 19B, 19C, 23A and 23B ("all vaccine-related serotypes") were somewhat reduced (Table 2 in [3]). These data establish that herd immunity from the use of PREVNAR® (7vPnC) in children under two years of age was modest for serotypes 6A and 19A, and provide a basis for the inclusion of serotypes 6A and 19A in the 13vPnC vaccine of this invention.

Conclusion for Addition of 6A and 19A

Figure 2:
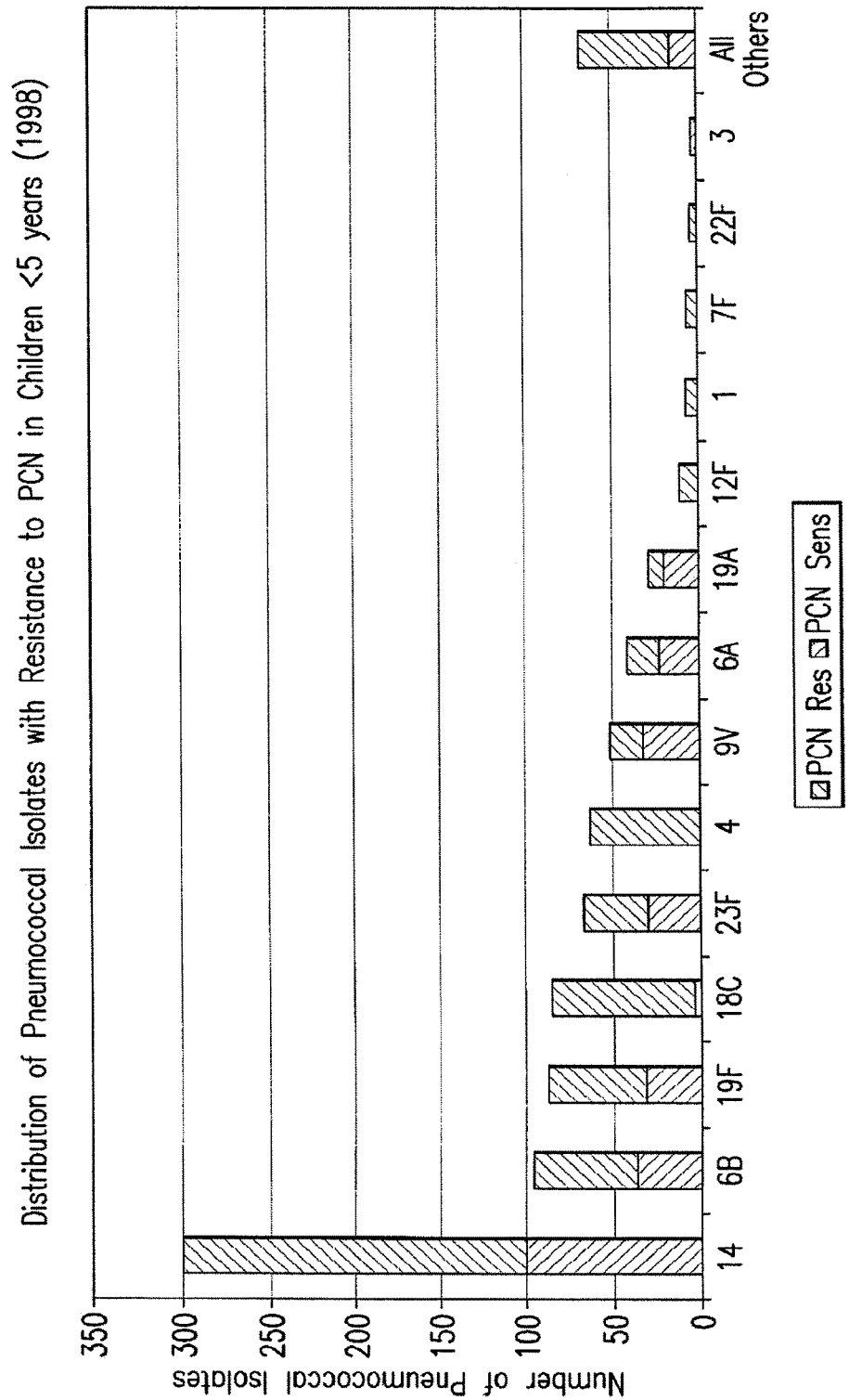
FIG. 2 depicts the distribution of pneumococcal isolates with resistance to penicillin (PCN) in children <5 years of age (1998).

The post-marketing surveillance data and the case-control study results noted in FIG. 1 and Table 2 with the 7vPnC vaccine suggest that, consistent with the other information on immune responses and performance in the animals models described above, there may be some cross-protection against 6A disease, but to a lesser extent than to 6B disease. Furthermore, it appears the protection against 19A is limited. Therefore, a 13vPnC vaccine containing serotypes 6A and 19A provides coverage that is not dependent on the limitations of serogroup cross-protection by serotypes 6B and 19F.

Accordingly, the present invention provides a multivalent immunogenic composition comprising 13 distinct polysaccharide-protein conjugates, wherein each of the conjugates contains a different capsular polysaccharide conjugated to a carrier protein, and wherein the capsular polysaccharides are prepared from serotypes 1, 3, 4, 5, 6A, 6B, 7F, 9V, 14, 18C, 19A, 19F and 23F of Streptococcus pneumoniae, together with a physiologically acceptable vehicle. One such carrier protein is the diphtheria toxoid designated $CRM_{197}$. The immunogenic composition may further comprise an adjuvant, such as an aluminum-based adjuvant, such as aluminum phosphate, aluminum sulfate and aluminum hydroxide.

Capsular polysaccharides are prepared by standard techniques known to those skilled in the art. In the present invention, capsular polysaccharides are prepared from serotypes 1, 3, 4, 5, 6A, 6B, 7F, 9V, 14, 18C, 19A, 19F and 23F of Streptococcus pneumoniae. These pneumococcal conjugates are prepared by separate processes and formulated into a single dosage formulation. For example, in one embodiment, each pneumococcal polysaccharide serotype is grown in a soy-based medium. The individual polysaccharides are then purified through centrifugation, precipitation, ultrafiltration, and column chromatography. The purified polysaccharides are chemically activated to make the saccharides capable of reacting with the carrier protein.

Once activated, each capsular polysaccharide is separately conjugated to a carrier protein to form a glycoconjugate. In one embodiment, each capsular polysaccharide is conjugated to the same carrier protein. In this embodiment, the conjugation is effected by reductive amination.

The chemical activation of the polysaccharides and subsequent conjugation to the carrier protein are achieved by conventional means. See, for example, U.S. Pat. Nos. 4,673, 574 and 4,902,506 [34, 35].

Carrier proteins are preferably proteins that are non-toxic and non-reactogenic and obtainable in sufficient amount and purity. Carrier proteins should be amenable to standard conjugation procedures. In a particular embodiment of the present invention, $CRM_{197}$ is used as the carrier protein.

$CRM_{197}$ (Wyeth, Sanford, N.C.) is a non-toxic variant (i.e., toxoid) of diphtheria toxin isolated from cultures of Corynebacterium diphtheria strain C7 (β197) grown in casamino acids and yeast extract-based medium. CRM₁₉₇ is purified through ultra-filtration, ammonium sulfate precipitation, and ion-exchange chromatography. Alternatively, CRM₁₉₇ is prepared recombinantly in accordance with U.S. Pat. No. 5,614,382, which is hereby incorporated by reference. Other diphtheria toxoids are also suitable for use as carrier proteins.

Other suitable carrier proteins include inactivated bacterial toxins such as tetanus toxoid, pertussis toxoid, cholera toxoid (e.g., as described in International Patent Application WO2004/083251 [38]), E. coli LT, E. coli ST, and exotoxin A from *Pseudomonas aeruginosa*. Bacterial outer membrane proteins such as outer membrane complex c (OMPC), porins, transferrin binding proteins, pneumolysin, pneumococcal surface protein A (PspA), pneumococcal adhesin protein (PsaA), C5a peptidase from Group A or Group B *streptococcus*, or *Haemophilus influenzae* protein D, can also be used. Other proteins, such as ovalbumin, keyhole limpet hemocyanin (KLH), bovine serum albumin (BSA) or purified protein derivative of tuberculin (PPD) can also be used as carrier proteins.

After conjugation of the capsular polysaccharide to the carrier protein, the polysaccharide-protein conjugates are purified (enriched with respect to the amount of polysaccharide-protein conjugate) by a variety of techniques. These techniques include concentration/diafiltration operations, precipitation/elution, column chromatography, and depth filtration. See examples below.

After the individual glycoconjugates are purified, they are compounded to formulate the immunogenic composition of the present invention, which can be used as a vaccine. Formulation of the immunogenic composition of the present invention can be accomplished using art-recognized methods. For instance, the 13 individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In certain embodiments, the immunogenic composition will comprise one or more adjuvants. As defined herein, an "adjuvant" is a substance that serves to enhance the immunogenicity of an immunogenic composition of this invention. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (PCT Publ. No. WO 90/14837), containing 5% Squalene, 0.5% Tween 80, and 0.5% Span 85 (optionally containing various amounts of MTP-PE (see below, although not required)) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL™) described in U.S. Pat. No. 4,912,094 (Corixa), trehalose dimycolate (TDM), and cell wall skeleton (CWS), preferably MPL+CWS (Detox™);

(3) saponin adjuvants, such as Quil A or STIMULON™ QS-21 (Antigenics, Framingham, Mass.) (U.S. Pat. No. 5,057,540) may be used or particles generated therefrom such as ISCOMs (immunostimulating complexes);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-Tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also know as 529 (formerly known as RC529), which is formulated as an aqueous form or as a stable emulsion, synthetic polynucleotides such as oligonucleotides containing CpG motif(s) (U.S. Pat. No. 6,207,646);

(5) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc.;

(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an E. coli heat-labile toxin (LT), particularly LT-K63, LT-R72, CT-S109, PT-K9/G129 (see, e.g., WO 93/13302 and WO 92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

The vaccine formulations of the present invention can be used to protect or treat a human susceptible to pneumococcal infection, by means of administering the vaccine via a systemic or mucosal route. These administrations can include injection via the intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage).

The amount of conjugate in each vaccine dose is selected as an amount that induces an immunoprotective response without significant, adverse effects. Such amount can vary depending upon the pneumococcal serotype. Generally, each dose will comprise 0.1 to 100 μg of polysaccharide, particularly 0.1 to 10 μg, and more particularly 1 to 5 μg.

Optimal amounts of components for a particular vaccine can be ascertained by standard studies involving observation of appropriate immune responses in subjects. Following an initial vaccination, subjects can receive one or several booster immunizations adequately spaced.

In a particular embodiment of the present invention, the 13vPnC vaccine is a sterile liquid formulation of pneumococcal capsular polysaccharides of serotypes 1, 3, 4, 5, 6A, 6B, 7F, 9V, 14, 18C, 19A, 19F, and 23F individually conjugated to $CRM_{197}$. Each 0.5 mL dose is formulated to contain: 2 μg of each saccharide, except for 6B at 4 μg; approximately 29 μg $CRM_{197}$ carrier protein; 0.125 mg of elemental aluminum (0.5 mg aluminum phosphate) adjuvant; and sodium chloride and sodium succinate buffer as excipients. The liquid is filled into single dose syringes without a preservative. After shaking, the vaccine is a homogeneous, white suspension ready for intramuscular administration.

The choice of dose level for the 13vPnC vaccine is similar to the marketed 7vPnC vaccine (PREVNAR®). The 2 μg saccharide dose level was selected for all serotypes, except for 6B, which is at 4 μg per dose. The 7vPnC vaccine has shown desirable safety, immunogenicity, and efficacy against IPD in the 2 μg saccharide dose level for serotypes 4, 9V, 14, 18C, 19F and 23F, and at the 4 μg dose for 6B.

The immunization schedule can follow that designated for the 7vPnC vaccine. For example, the routine schedule for infants and toddlers against invasive disease caused by S. pneumoniae due to the serotypes included in the 13vPnC vaccine is 2, 4, 6 and 12-15 months of age. The compositions of this invention are also suitable for use with older children, adolescents and adults.

The compositions of this invention may further include one or more additional antigens for use against otitis media caused by infection with other bacteria. Such bacteria include nontypable *Haemophilus* influenza, *Moraxella catarrhalis* (formerly known as *Branhamella catarrhalis*) and *Alloiococcus otitidis*.

Examples of nontypable *Haemophilus influenzae* antigens suitable for inclusion include the P4 protein, also known as protein "e" (U.S. Pat. No. 5,601,831; International Patent Application WO03/078453), the P6 protein, also known as the PAL or the PBOMP-1 protein (U.S. Pat. No. 5,110,908; International Patent Application WO0100790), the P5 protein (U.S. Reissue Pat. No. 37,741), the *Haemophilus* adhesion and penetration protein (U.S. Pat. Nos. 6,245,337 and 6,676,948), the LKP tip adhesin protein (U.S. Pat. No. 5,643,725) and the NucA protein (U.S. Pat. No. 6,221,365).

Examples of *Moraxella catarrhalis* antigens suitable for inclusion include the UspA2 protein (U.S. Pat. Nos. 5,552,146, 6,310,190), the CD protein (U.S. Pat. No. 5,725,862), the E protein (U.S. Pat. No. 5,948,412) and the 74 kilodalton outer membrane protein (U.S. Pat. No. 6,899,885).

Examples of *Alloiococcus otitidis* antigens suitable for inclusion include those identified in International Patent Application WO03/048304.

The compositions of this invention may also include one or more proteins from *Streptococcus pneumoniae*. Examples of *Streptococcus pneumoniae* proteins suitable for inclusion include those identified in International Patent Application WO02/083855, as well as that described in International Patent Application WO02/053761.

The compositions of this invention may further include one or more proteins from *Neisseria meningitidis* type B. Examples of *Neisseria meningitidis* type B proteins suitable for inclusion include those identified in International Patent Applications WO03/063766, WO2004/094596, WO01/85772, WO02/16612 and WO01/87939.

The above disclosure generally describes the present invention. A more complete understanding can be obtained by reference to the following specific examples. These examples are described solely for the purpose of illustration and are not intended to limit the scope of the invention.

EXAMPLES

Example 1

Preparation of S. *Pneumoniae* Capsular Polysaccharide Serotype 1

Preparation of Master and Working Cell Banks

*S. pneumoniae* serotype 1 was obtained from the American Type Culture Collection, ATCC, strain 6301. Several generations of seed stocks were created in order to expand the strain and remove components of animal origin (generations F1, F2, and F3). Two additional generations of seed stocks were produced. The first additional generation was made from an F3 vial, and the subsequent generation was made from a vial of the first additional generation. Seed vials were stored frozen (<-70° C.) with synthetic glycerol as a cryopreservative. In addition to frozen vials, lyophilized vials were prepared for the F4 generation. For cell bank preparation, all cultures were grown in a soy-based medium. Prior to freezing, cells were concentrated by centrifugation, spent medium was removed, and cell pellets were resuspended in fresh medium containing a cryopreservative, such as synthetic glycerol.

Fermentation and Harvesting

Cultures from the working cell bank were used to inoculate seed bottles containing a soy-based medium. The bottles were incubated at 36° C.±2° C. without agitation until growth requirements were met. A seed bottle was used to inoculate a seed fermentor containing soy-based medium. A pH of about 7.0 was maintained with sterile sodium carbonate solution. After the target optical density was reached, the seed fermentor was used to inoculate the production fermentor containing soy-based medium. The pH was maintained with sterile sodium carbonate solution. The fermentation was terminated after cessation of growth or when the working volume of the fermentor was reached. An appropriate amount of sterile 12% deoxycholate sodium was added to the culture to lyse the bacterial cells and release cell-associated polysaccharide. After lysing, the fermentor contents were cooled. The pH of the lysed culture broth was adjusted to approximately pH 6.6 with acetic acid. The lysate was clarified by continuous flow centrifugation followed by depth filtration and 0.45 μm microfiltration.

In an alternate process, the fermentation pH of about 7.0 was maintained with 3N NaOH. After the target optical density was reached, the seed fermentor was used to inoculate the production fermentor containing soy-based medium. The pH was maintained with 3N NaOH. The fermentation was terminated after cessation of growth or when the working volume of the fermentor was reached. An appropriate amount of sterile 12% deoxycholate sodium was added to the culture to obtain a 0.12% concentration in the broth, to lyse the bacterial cells and release cell-associated polysaccharide. After lysing, the fermentor contents were held, with agitation, for a time interval between 8 and 24 hours at a temperature between 7° C. and 13° C., to assure that complete cellular lysis and polysaccharide release had occurred. Agitation during this hold period prevented lysate sediment from settling on the fermentor walls and pH probe, thereby allowing the pH probe integrity to be maintained.

Next, the pH of the lysed culture broth was adjusted to approximately pH 5.0 with 50% acetic acid. After a hold time without agitation, for a time interval between 12 and 24 hours at a temperature between 15° C. and 25° C., a significant portion of the previously soluble proteins dropped out of solution as a solid precipitate with little loss or degradation of the polysaccharide, which remained in solution. The solution with the precipitate was then clarified by continuous flow centrifugation followed by depth filtration and 0.45 μm microfiltration.

Purification

The purification of the pneumococcal polysaccharide consisted of several concentration/diafiltration operations, precipitation/elution, column chromatography, and depth filtration steps. All procedures were performed at room temperature unless otherwise specified.

Clarified broth from the fermentor cultures of *S. pneumoniae* serotype 1 were concentrated and diafiltered using a 100 kDa MWCO (kilodalton molecular weight cutoff) filter. Diafiltration was accomplished using sodium phosphate buffer at neutral pH. Diafiltration removed the low molecular weight medium components from the higher molecular weight biopolymers such as nucleic acid, protein and polysaccharide.

The polysaccharide was precipitated from the concentrated and diafiltered solution by adding hexadecyltrimethyl ammonium bromide (HB) from a stock solution to give a final concentration of 1% HB (w/v). The polysaccharide/HB precipitate was captured on a depth filter and the filtrate was discarded. The polysaccharide precipitate was resolubilized and eluted by recirculating a sodium chloride solution through the precipitate-containing depth filter. The filters were then rinsed with additional sodium chloride solution.

Sodium iodide (NaI) was added to the polysaccharide solution from a stock NaI solution to achieve a final concentration of 0.5% to precipitate HB. The precipitate was removed by depth filtration. The filtrate contains the target polysaccharide. The precipitation vessel and the filter were rinsed with a NaCl/NaI solution and the rinse was combined with the partially purified polysaccharide solution. The filter was discarded. The polysaccharide was then filtered through a 0.2 μm filter.

The polysaccharide solution was concentrated on a 30 kDa MWCO ultrafilter and diafiltered with a sodium chloride solution.

The partially purified polysaccharide solution was further purified by filtration through a depth filter impregnated with activated carbon. After filtration, the carbon filter was rinsed with a sodium chloride solution. The rinse is combined with the polysaccharide solution, which is then filtered through a 0.2 μm filter.

The polysaccharide solution was concentrated on a 30 kDa MWCO ultrafilter and adjusted with a 1M sodium phosphate buffer to achieve a final concentration of 0.025 M sodium phosphate. The pH was checked and adjusted to 7.0±0.2.

The ceramic hydroxyapatite (HA) column was equilibrated with sodium phosphate buffer containing sodium chloride to obtain the appropriate conductivity (<15 μS). The polysaccharide solution was then loaded onto the column. Under these conditions, impurities bound to the resin and the polysaccharide was recovered in the flow-through from the column. The polysaccharide solution was filtered through 0.2 μm inline filters located before and after the column.

The polysaccharide solution was concentrated using a 30 kDa MWCO filter. The concentrate was then diafiltered with Water for Injection (WFI).

The diafiltered polysaccharide solution was filtered through a 0.2 μm membrane filter into polypropylene bottles. Samples were removed for release testing and the purified polysaccharide was stored frozen at −25°±5° C.

Characterization

The 1H-NMR data was consistent with the chemical structure by the assignment of signals assigned to the protons of the polysaccharide molecule. The 1H-NMR spectrum showed a series of well-resolved signals (protons from the methyl group) for the quantitation of the O-acetyl functional group in the polysaccharide.

The identity of the monovalent polysaccharide was confirmed by countercurrent immunoelectrophoresis using specific antisera.

High performance gel filtration chromatography coupled with refractive index and multiangle laser light scattering (MALLS) detectors was used in conjunction with the sample concentration to calculate the molecular weight.

Size exclusion chromatography media (CL-4B) was used to profile the relative molecular size distribution of the polysaccharide.

Example 2

Preparation of Serotype 1 Pneumococcal Saccharide-CRM$_{197}$ Conjugate

Activation and Conjugation

Containers of purified polysaccharide were thawed and combined in a reaction vessel. To the vessel, 0.2 M sodium carbonate, pH 9.0 was added for partial deacetylation (hydrolysis) for 3 hours at 50° C. The reaction was cooled to 20° C. and neutralization was performed by 0.2 M acetic acid. Oxidation in the presence of sodium periodate was performed by incubation at 2-8° C., and the mixture was stirred for 15-21 hours.

The activation reaction mixture was concentrated and diafiltered 10× with 0.9% NaCl using a 30K MWCO membrane. The retentate was 0.2 μm filtered. The activated saccharide was filled into 100 mL glass lyophilization bottles and shell-frozen at −75° C. and lyophilized.

"Shell-freezing" is a method for preparing samples for lyophilization (freeze-drying). Flasks are automatically rotated by motor driven rollers in a refrigerated bath containing alcohol or any other appropriate fluid. A thin coating of product is evenly frozen around the inside "shell" of a flask, permitting a greater volume of material to be safely processed during each freeze-drying run. These automatic, refrigerated units provide a simple and efficient means of pre-freezing many flasks at a time, producing the desired coatings inside, and providing sufficient surface area for efficient freeze-drying.

Bottles of lyophilized material were brought to room temperature and resuspended in CRM$_{197}$ solution at a saccharide/protein ratio of 2:1. To the saccharide/protein mixture 1M sodium phosphate buffer was added to a final 0.2M ionic strength and a pH of 7.5, then sodium cyanoborohydride was added. The reaction was incubated at 23° C. for 18 hours, followed by a second incubation at 37° C. for 72 hours. Following the cyanoborohydride incubations, the reaction mixture was diluted with cold saline followed by the addition of 1M sodium carbonate to adjust the reaction mixture to pH 9.0. Unreacted aldehydes were quenched by addition of sodium borohydride by incubation at 23° C. for 3-6 hours.

The reaction mixture was diluted 2-fold with saline and transferred through a 0.45-5 µm prefilter into a retentate vessel. The reaction mixture is diafiltered 30× with 0.15 M phosphate buffer, pH 6, and 20× with saline. The retentate was filtered through a 0.2 µm filter.

The conjugate solution was diluted to a target of 0.5 mg/mL in 0.9% saline, and then sterile filtered into final bulk concentrate (FBC) containers in a Class 100 hood. The conjugate was stored at 2-8° C.

Characterization

Size exclusion chromatography media (CL-4B) was used to profile the relative molecular size distribution of the conjugate.

The identity of the conjugate was confirmed by the slot-blot assay using specific antisera.

The saccharide and protein concentrations were determined by the uronic acid and Lowry assays, respectively. The ratio of saccharide to protein in the covalently bonded conjugate complex was obtained by the calculation:

$$\text{Ratio} = \frac{\mu g/mL \text{ saccharide}}{\mu g/mL \text{ protein}}$$

O-acetyl content was measured by the Hestrin method (Hestrin et. al., J. Biol. Chem. 1949, 180, p. 249). The ratio of 0-acetyl concentration to total saccharide concentration gave µmoles of 0-acetyl per mg of saccharide.

Example 3

Preparation of S. Pneumoniae Capsular Polysaccharide Serotype 3

Preparation of Master and Working Cell Banks

S. pneumoniae serotype 3 was obtained from Dr. Robert Austrian, University of Pennsylvania, Philadelphia, Pa. For preparation of the cell bank system, see Example 1.

Fermentation and Harvesting

Cultures from the working cell bank were used to inoculate seed bottles containing soy-based medium. The bottles were incubated at 36° C.±2° C. without agitation until growth requirements were met. A seed bottle was used to inoculate a seed fermentor containing soy-based medium. A pH of about 7.0 was maintained with sterile sodium carbonate solution. After the target optical density was reached, the seed fermentor was used to inoculate an intermediate seed fermentor. After the target optical density was reached, the intermediate seed fermentor was used to inoculate the production fermentor. The pH was maintained with sterile sodium carbonate solution. The fermentation was terminated after the working volume of the fermentor was reached. An appropriate amount of sterile 12% sodium deoxycholate was added to the culture to lyse the bacterial cells and release cell-associated polysaccharide. After lysing, the fermentor contents were cooled. The pH of the lysed culture broth was adjusted to approximately pH 6.6 with acetic acid. The lysate was clarified by continuous flow centrifugation followed by depth filtration and 0.45 µm microfiltration.

Purification

The purification of the pneumococcal polysaccharide consisted of several concentration/diafiltration operations, precipitation/elution, column chromatography, and depth filtration steps. All procedures were performed at room temperature unless otherwise specified.

Clarified broth from the fermentor cultures of S. pneumoniae serotype 3 were concentrated and diafiltered using a 100 kDa MWCO filter. Diafiltration was accomplished using sodium phosphate buffer at neutral pH. Diafiltration removed the low molecular weight medium components from the higher molecular weight biopolymers such as nucleic acid, protein and polysaccharide.

Prior to the addition of hexadecyltrimethyl ammonium bromide (HB), a calculated volume of a NaCl stock solution was added to the concentrated and diafiltered polysaccharide solution to give a final concentration of 0.25 M NaCl. The polysaccharide was then precipitated by adding HB from a stock solution to give a final concentration of 1% HB (w/v). The polysaccharide/HB precipitate was captured on a depth filter and the filtrate was discarded. The polysaccharide precipitate was resolubilized and eluted by recirculating a sodium chloride solution through the precipitate-containing depth filter. The filters were then rinsed with additional sodium chloride solution.

Sodium iodide (NaI) was added to the polysaccharide solution from a stock NaI solution to achieve a final concentration of 0.5% to precipitate HB. The precipitate was removed by depth filtration. The filtrate contained the target polysaccharide. The precipitation vessel and the filter were rinsed with a NaCl/NaI solution and the rinse was combined with the partially purified polysaccharide solution. The filter was discarded. The polysaccharide was then filtered through a 0.2 µm filter.

The polysaccharide solution was concentrated on a 30 kDa MWCO ultrafilter and diafiltered with a sodium chloride solution.

The partially purified polysaccharide solution was further purified by filtration through a depth filter impregnated with activated carbon. After filtration, the carbon filter was rinsed with a sodium chloride solution. The rinse was combined with the polysaccharide solution, which was then filtered through a 0.2 µm filter.

The polysaccharide solution was concentrated on a 30 kDa MWCO ultrafilter and adjusted with a 1M sodium phosphate buffer to achieve a final concentration of 0.025M sodium phosphate. The pH was checked and adjusted to 7.0±0.2.

The ceramic hydroxyapatite (HA) column was equilibrated with sodium phosphate buffer containing sodium chloride to obtain the appropriate conductivity (15 µS). The polysaccharide solution was then loaded onto the column. Under these conditions, impurities bound to the resin and the polysaccharide was recovered in the flow-through from the column. The polysaccharide was flushed through the column with buffer and was filtered through a 0.2 µm filter.

The polysaccharide solution was concentrated using a 30 kDa MWCO filter. The concentrate was then diafiltered with WFI.

The diafiltered polysaccharide solution was filtered through a 0.2 µm membrane filter into stainless steel containers. Samples were removed for release testing and the purified polysaccharide was stored frozen at −25°±5° C.

Characterization

The 1H-NMR data was consistent with the chemical structure by the assignment of signals assigned to the protons of the polysaccharide molecule.

The identity of the monovalent polysaccharide was confirmed by countercurrent immunoelectrophoresis using specific antisera.

High performance gel filtration chromatography, coupled with refractive index and multiangle laser light scattering (MALLS) detectors, was used in conjunction with the sample concentration to calculate the molecular weight.

Size exclusion chromatography media (CL-4B) was used to profile the relative molecular size distribution of the polysaccharide.

Example 4

Preparation of Serotype 3 Pneumococcal Saccharide-CRM$_{197}$ Conjugate

Activation and Conjugation

Containers of purified serotype 3 saccharide were thawed and combined in a reaction vessel. To the vessel, WFI and 2M acetic acid were added to a final concentration of 0.2M and 2 mg/mL saccharide. The temperature of the solution was raised to 85° C. for one hour to hydrolyze the polysaccharide. The reaction was cooled to ≤25° C. and 1M magnesium chloride was added to a final concentration of 0.1M. Oxidation in the presence of sodium periodate was performed by incubation for 16-24 hours at 23° C.

The activation reaction mixture was concentrated and diafiltered 10× with WFI using a 100K MWCO membrane. The retentate was filtered through a 0.2-µm filter.

For compounding, 0.2M sodium phosphate, pH 7.0, was added to the activated saccharide to a final concentration of 10 mM and a pH of 6.0-6.5. CRM$_{197}$ carrier protein was mixed with the saccharide solution to a ratio of 2 g of saccharide per 1 g of CRM$_{197}$. The combined saccharide/protein solution was filled into 100 mL glass lyophilization bottles with a 50 mL target fill, shell-frozen at −75° C., and lyophilized.

Bottles of co-lyophilized saccharide/protein material were brought to room temperature and resuspended in 0.1M sodium phosphate buffer, pH 7.0, to a final saccharide concentration of 20 mg/mL. The pH was adjusted to 6.5 and then a 0.5 molar equivalent of sodium cyanoborohydride was added. The reaction was incubated at 37° C. for 48 hours. Following the cyanoborohydride incubation, the reaction mixture was diluted with cold 5 mM succinate/0.9% saline buffer. Unreacted aldehydes were quenched by the addition of sodium borohydride and incubation at 23° C. for 3-6 hours. The reaction mixture was transferred through a 0.45-5 µm prefilter into a retentate vessel.

The reaction mixture was diafiltered 30× with 0.1M phosphate buffer (pH 9), 20× with 0.15M phosphate butter (pH 6), and 20× with 5 mM succinate/0.9% saline. The retentate was filtered through a 0.2-µm filter.

The conjugate solution was diluted to a saccharide target of 0.5 mg/mL, and then sterile filtered into FBC containers in a Class 100 hood. The conjugate was stored at 2-8° C.

Characterization

Size exclusion chromatography media (CL-4B) was used to profile the relative molecular size distribution of the conjugate.

The identity of the conjugate was confirmed by the slot-blot assay using specific antisera.

The saccharide and protein concentrations were determined by the Anthrone and Lowry assays, respectively. The ratio of saccharide to protein in the covalently bonded conjugate complex was obtained by the calculation:

$$\text{Ratio} = \frac{\mu g/mL \text{ saccharide}}{\mu g/mL \text{ protein}}$$

Example 5

Preparation of S. Pneumoniae Capsular Polysaccharide Serotype 5

S. pneumoniae serotype 5 was obtained from Dr. Gerald Schiffman of the State University of New York, Brooklyn, N.Y. For preparation of the cell bank system, see Example 1. For fermentation, harvesting, purification and characterization of the polysaccharide, see Example 1.

Alternate Fermentation Process

Cultures from the working cell bank were used to inoculate seed bottles containing a soy-based medium and a 10 mM sterile NaHCO$_3$ solution. The bottles were incubated at 36° C.±2° C. without agitation until growth requirements were met. A seed bottle was used to inoculate a seed fermentor containing soy-based medium and a 10 mM sterile NaHCO$_3$ solution. A pH of about 7.0 was maintained with 3N NaOH. After the target optical density was reached, the seed fermentor was used to inoculate the production fermentor containing soy-based medium with a 10 mM NaHCO$_3$ concentration. The pH was maintained with 3N NaOH. The fermentation was terminated after cessation of growth or when the working volume of the fermentor was reached. An appropriate amount of sterile 12% sodium deoxycholate was added to the culture to obtain a 0.12% concentration in the broth, to lyse the bacterial cells and release cell-associated polysaccharide. After lysing, the fermentor contents were held, with agitation, for a time interval between 8 and 24 hours at a temperature between 7° C. and 13° C. to assure that complete cellular lysis and polysaccharide release had occurred. Agitation during this hold period prevented lysate sediment from settling on the fermentor walls and pH probe, thereby allowing the pH probe integrity to be maintained. Next, the pH of the lysed culture broth was adjusted to approximately pH 4.5 with 50% acetic acid. After a hold time without agitation, for a time interval between 12 and 24 hours at a temperature between 15° C. and 25° C., a significant portion of the previously soluble proteins dropped out of solution as a solid precipitate with little loss or degradation of the polysaccharide, which remained in solution. The solution with the precipitate was then clarified by continuous flow centrifugation followed by depth filtration and 0.45 μm microfiltration.

Example 6

Preparation of Serotype 5 Pneumococcal Saccharide-CRM$_{197}$ Conjugate

Activation and Conjugation

Containers of serotype 5 saccharide were thawed and combined in a reaction vessel. To the vessel, 0.1M sodium acetate, pH 4.7, was added followed by oxidation in the presence of sodium periodate by incubation for 16-22 hours at 23° C.

The activation reaction mixture was concentrated and diafiltered 10× with WFI using a 100K MWCO membrane. The retentate was filtered through a 0.2 μm filter.

The serotype 5 activated saccharide was combined with CRM$_{197}$ at a ratio of 0.8:1. The combined saccharide/protein solution was filled into 100 mL glass lyophilization bottles (50 mL target fill), shell-frozen at −75° C., and co-lyophilized.

Bottles of co-lyophilized material were brought to room temperature and resuspended in 0.1M sodium phosphate, pH 7.5, and sodium cyanoborohydride was added. The reaction was incubated at 30° C. for 72 hours, followed by a second addition of cyanoborohydride and incubated at 30° C. for 20-28 hours.

Following the cyanoborohydride incubations, the reaction mixture was diluted 2-fold with saline and transferred through a 0.45-5 μm prefilter into a retentate vessel. The reaction mixture was diafiltered 30× with 0.01 M phosphate buffer, pH 8, 20× with 0.15M phosphate buffer, pH 6, and 20× with saline. The retentate was filtered through a 0.2 μm filter.

The conjugate solution was diluted to a saccharide target of 0.5 mg/mL, and then sterile filtered into FBC containers in a Class 100 hood. The conjugate was stored at 2-8° C.

For the characterization of the conjugate, see Example 2.

Example 7

Preparation of S. Pneumoniae Capsular Polysaccharide Serotype 6A

S. pneumoniae serotype 6A was obtained from Dr. Gerald Schiffman of the State University of New York, Brooklyn, N.Y. For preparation of the cell bank system, see Example 1. For fermentation, harvesting and purification of the polysaccharide, see Example 1, except that during purification, the 30 kDa MWCO concentration step, prior to the chromatography step, is omitted.

Example 8

Preparation of Serotype 6A Pneumococcal Saccharide-CRM$_{197}$ Conjugate

Activation and Conjugation

Serotype 6A polysaccharide is a high molecular weight polymer that had to be reduced in size prior to oxidation. Containers of serotype 6A saccharide were thawed and combined in a reaction vessel. To the vessel, 2 M acetic acid was added to a final concentration of 0.1 M for hydrolysis for 1.5 hours at 60° C. The reaction was cooled to 23° C. and neutralization was performed by adjusting the reaction mixture with 1 M NaOH to pH 6. Oxidation in the presence of sodium periodate was performed by incubation at 23° C. for 14-22 hours.

The activation reaction mixture was concentrated and diafiltered 10× with WFI using a 100K MWCO membrane. The retentate was filtered through a 0.2 μm filter.

Serotype 6A was compounded with sucrose and filled into 100 mL glass lyophilization bottles (50 mL target fill) and shell-frozen at −75° C. and lyophilized.

Bottles of lyophilized material were brought to room temperature and resuspended in dimethylsulfoxide (DMSO) at a saccharide/protein ratio of 1:1. After addition of sodium cyanoborohydride, the reaction mixture was incubated at 23° C. for 18 hours. Following the cyanoborohydride incubation, the reaction mixture was diluted with cold saline. Unreacted aldehydes were quenched by addition of sodium borohydride by incubation at 23° C. for 3-20 hours.

The diluted reaction mixture was transferred through a 5 μm prefilter into a retentate vessel. The reaction mixture was diafiltered 10× with 0.9% NaCl and 30× with succinate-buffered NaCl. The retentate was filtered through a 0.2 μm filter. The conjugate solution was diluted to a saccharide target of 0.5 mg/mL, and then sterile filtered into FBC containers in a Class 100 hood. The conjugate was stored at 2-8° C.

For the characterization of the conjugate, see Example 2.

Example 9

Preparation of S. Pneumoniae Capsular Polysaccharide Serotype 7F

S. pneumoniae serotype 7F was obtained from Dr. Gerald Schiffman of the State University of New York, Brooklyn, N.Y. For preparation of the cell bank system, and for fermentation and harvesting of the polysaccharide, see Example 3. For an alternate fermentation and harvesting process, see the alternate process described in Example 1.

Purification

The purification of the pneumococcal polysaccharide consisted of several concentration/diafiltration operations, precipitation/elution, column chromatography, and depth filtration steps. All procedures were performed at room temperature unless otherwise specified.

Clarified broth from fermentor cultures of S. pneumoniae serotype 7F were concentrated and diafiltered using a 100 kDa MWCO filter. Diafiltration was accomplished using sodium phosphate buffer at neutral pH. Diafiltration removed the low molecular weight medium components from the higher molecular weight biopolymers such as nucleic acid, protein and polysaccharide.

Serotype 7F does not form a precipitate with HB. Instead, impurities were precipitated from the concentrated and diafiltered solution by adding the HB from a stock solution to a final concentration of 1% HB. The precipitate was captured on a depth filter and the filter was discarded. The polysaccharide was contained in the filtrate.

Sodium iodide (NaI) was added to the polysaccharide solution from a stock NaI solution to achieve a final concentration of 0.5% to precipitate HB. The precipitate was removed by depth filtration. The filtrate contained the target polysaccharide. The precipitation vessel and the filter were rinsed with a NaCl/NaI solution and the rinses were combined with the partially purified polysaccharide solution.

The filter was discarded. The polysaccharide was then filtered through a 0.2 µm filter.

The polysaccharide solution was concentrated on a 30 kDa MWCO ultrafilter and diafiltered with a sodium chloride solution.

The partially purified polysaccharide solution was further purified by filtration through a depth filter impregnated with activated carbon. After filtration, the carbon filter was rinsed with a sodium chloride solution. The rinse was combined with the polysaccharide solution, which was then filtered through a 0.2 µm filter.

The polysaccharide solution was concentrated on a 30 kDa MWCO ultrafilter and adjusted with a 1M sodium phosphate buffer to achieve a final concentration of 0.025M sodium phosphate. The pH was checked and adjusted to 7.0±0.2.

The ceramic hydroxyapatite (HA) column was equilibrated with sodium phosphate buffer containing sodium chloride to obtain the appropriate conductivity (15 µS). The polysaccharide solution was then loaded onto the column. Under these conditions, impurities bound to the resin and the polysaccharide was recovered in the flow-through from the column. The polysaccharide was flushed through the column with buffer and was filtered through a 0.2 µm filter.

The polysaccharide solution was concentrated using a 30 kDa MWCO filter. The concentrate was then diafiltered with WFI.

The diafiltered polysaccharide solution was filtered through a 0.2 µm membrane filter into stainless steel containers. Samples were removed for release testing and the purified polysaccharide was stored at 2°-8° C.

For characterization of the polysaccharide, see Example 3.

Example 10

Preparation of Serotype 7F Pneumococcal Saccharide-CRM$_{197}$ Conjugate

Activation and Conjugation

Oxidation in the presence of sodium periodate was performed by incubation for 16-24 hrs at 23° C.

The activation reaction mixture was concentrated and diafiltered 10× with 10 mM NaOAc, pH 4.5, using a 100K MWCO membrane. The retentate was filtered through a 0.2 µm filter.

Serotype 7F was filled into 100 mL glass lyophilization bottles (50 mL target fill) and shell-frozen at −75° C. and lyophilized.

Bottles of lyophilized serotype 7F and CRM$_{197}$ were brought to room temperature and resuspended in DMSO at a saccharide/protein ratio of 1.5:1. After the addition of sodium cyanoborohydride, the reaction was incubated at 23° C. for 8-10 hours. Unreacted aldehydes were quenched by the addition of sodium borohydride by incubation at 23° C. for 16 hours.

The reaction mixture was diluted 10-fold with cold saline and transferred through a 5 µm prefilter into a retentate vessel. The reaction mixture was diafiltered 10× with 0.9% saline and 30× with succinate-buffered saline. The retentate was filtered through a 0.2 µm filter.

The conjugate solution was diluted to a saccharide target of 0.5 mg/mL 0.9% saline, and then sterile filtered into FBC containers in a Class 100 hood. The conjugate was stored at 2-8° C.

For characterization of the conjugate, see Example 4.

Example 11

Preparation of S. Pneumoniae Capsular Polysaccharide Serotype 19A

S. pneumoniae serotype 19A was obtained from Dr. Gerald Schiffman of the State University of New York, Brooklyn, N.Y. For preparation of the cell bank system, see Example 1. For fermentation, harvesting and purification of the polysaccharide, see Example 7. For characterization, see Example 3.

Example 12

Preparation of Serotype 19A Pneumococcal Saccharide-CRM$_{197}$ Conjugate

Activation and Conjugation

Containers of serotype 19A saccharide were thawed and combined in a reaction vessel. Sodium acetate was added to 10 mM (pH 5.0) and oxidation was carried out in the presence of sodium periodate by incubation for 16-24 hrs at 23° C.

The activation reaction mixture was concentrated and diafiltered 10× with 10 mM acetate, pH 5.0, using a 100K MWCO membrane. The retentate was filtered through a 0.2 µm filter.

The activated saccharide was compounded with sucrose followed by the addition of CRM$_{197}$. The serotype 19A activated saccharide and CRM$_{197}$ mixture (0.8:1 ratio) was filled into 100 mL glass lyophilization bottles (50 mL target fill) and shell-frozen at −75° C. and lyophilized.

Bottles of lyophilized material were brought to room temperature and resuspended in DMSO. To the saccharide/protein mixture, sodium cyanoborohydride (100 mg/ml) was added. The reaction was incubated at 23° C. for 15 hours. Following the cyanoborohydride incubation, unreacted aldehydes were quenched by the addition of sodium borohydride by incubation at 23° C. for 3-20 hours.

The reaction mixture was diluted 10-fold with cold saline and transferred through a 5 µm prefilter into a retentate vessel. The reaction mixture was diafiltered 10× with 0.9% NaCl, 0.45-µm filtered, and 30× with diafiltration using 5 mM succinate/0.9% NaCl buffer, pH 6. The retentate was filtered through a 0.2 µm filter.

The conjugate solution was diluted to a target of 0.5 mg/mL using 5 mM succinate/0.9% saline, and then sterile filtered into FBC containers in a Class 100 hood. The conjugate was stored at 2-8° C.

For characterization of the conjugate, see Example 4.

Example 13

Preparation of S. Pneumoniae Capsular Polysaccharide Serotypes 4, 6B, 9V, 14, 18C, 19F and 23F Preparation of the S. pneumoniae Seed Culture S. pneumoniae serotypes 4, 6B, 9V, 18C, 19F and 23F were obtained from Dr. Gerald Schiffman, State University of New York, Brooklyn, N.Y. *S. pneumoniae* serotype 14 was obtained from the ATCC, strain 6314.

Separately, one vial of each of the desired serotypes of *Streptococcus pneumoniae* was used to start a fermentation batch. Two bottles containing a soy-based medium and phenol red were adjusted to a pH range of 7.4±0.2 using sodium carbonate, and the required volume of 50% dextrose/1% magnesium sulfate solution was then added to the bottles. The two bottles were inoculated with different amounts of seed. The bottles were incubated at 36°±2° C. until the medium turned yellow. Following incubation, samples were removed from each bottle and tested for optical density (OD) (0.3 to 0.9) and pH (4.6 to 5.5). One of the two bottles was selected for inoculation of the seed fermentor.

Soy-based medium was transferred to the seed fermentor and sterilized. Then a volume of 50% dextrose/1% magnesium sulfate solution was added to the fermentor. The pH and agitation of the seed fermentor were monitored and controlled (pH 6.7 to 7.4). The temperature was maintained at 36°±2° C. The seed inoculum (bottle) was aseptically connected to the seed fermentor and the inoculum was transferred. The fermentor was maintained in pH control and samples were periodically removed and tested for OD and pH. When the desired OD of 0.5 at 600 nm was reached, the intermediate fermentor was inoculated with the fermentation broth from the seed fermentor.

Soy-based medium was transferred to the intermediate fermentor and sterilized. Then a volume of 50% dextrose/1% magnesium sulfate solution was added to the fermentor. The pH and agitation of the intermediate fermentor were monitored and controlled (pH 6.7 to 7.4). The temperature was maintained at 36°±2° C. The contents of the seed fermentor were transferred to the intermediate fermentor. The fermentor was maintained in pH control and samples were periodically removed and tested for OD and pH. When the desired OD of 0.5 at 600 nm was reached, the production fermentor was inoculated with the fermentation broth from the intermediate fermentor.

Soy-based medium was transferred to the production fermentor and sterilized. Then a volume of 50% dextrose/1% magnesium sulfate solution was added to the fermentor. The pH and agitation of the production fermentor were monitored and controlled (pH 6.7 to 7.4). The temperature was maintained at 36°±2° C. The fermentor was maintained in pH control and samples were periodically removed and tested for OD and pH, until the fermentation was complete.

Deoxycholate sodium was added to the fermentor to a final concentration of approximately 0.12% w/v. The culture was mixed for a minimum of thirty minutes and the temperature set point was reduced to 10° C. The culture was incubated overnight and following confirmation of inactivation, the pH of the culture was adjusted to between 6.4 and 6.8, as necessary, with 50% acetic acid. The temperature of the fermentor was increased to 20°±5° C. and the contents were transferred to the clarification hold tank.

The contents of the clarification hold tank (including the cellular debris) were processed through a centrifuge at a flow rate between 25 and 600 liters per hour (except Serotype 4, wherein the cell debris was discarded and the flow rate tightened to between 25 and 250 liters per hour). Samples of the supernatant were removed and tested for OD. The desired OD during the centrifugation was 0.15.

Initially, the supernatant was recirculated through a depth filter assembly until an OD of 0.05±0.03 was achieved. Then the supernatant was passed through the depth filter assembly and through a 0.45 μm membrane filter to the filtrate hold tank.

Subsequently, the product was transferred through closed pipes to the purification area for processing.

All of the above operations (centrifugation, filtration and transfer) were performed between 10° C. to 30° C.

For an alternate fermentation and harvesting process for serotypes 4 and 6B, see the alternate process described in Example 1.

Purification

The purification of each pneumococcal polysaccharide consisted of several concentration/diafiltration operations, precipitation/elution, column chromatography, and depth filtration steps. All procedures were performed at room temperature unless otherwise specified.

Clarified broth from the fermentor cultures of the desired *S. pneumoniae* serotype was concentrated and diafiltered using a 100 kDa MWCO filter. Diafiltration was accomplished using sodium phosphate buffer at pH<9.0. Diafiltration removed the low molecular weight medium components from the higher molecular weight biopolymers such as nucleic acid, protein and polysaccharide.

The polysaccharide was precipitated from the concentrated and diafiltered solution by adding HB from a stock solution to give a final concentration of 1% HB (w/v) (except Serotype 23F, which had a final concentration of 2.5%). The polysaccharide/HB precipitate was captured on a depth filter and the filtrate was discarded. (Note: Serotype 14 does not precipitate; therefore the filtrate was retained.) The polysaccharide precipitate was resolubilized and eluted by recirculating a sodium chloride solution through the precipitate-containing depth filter. The filters were then rinsed with additional sodium chloride solution.

Sodium iodide (NaI) was added to the polysaccharide solution from a stock NaI solution to achieve a final concentration of 0.5% to precipitate HB (except for Serotype 6B, which had a final concentration of 0.25%). The precipitate was removed by depth filtration. The filtrate contained the target polysaccharide. The filter was discarded. The polysaccharide was then filtered through a 0.2 μm filter.

The polysaccharide solution was concentrated on a 30 kDa MWCO ultrafilter and diafiltered with a sodium chloride solution.

The partially purified polysaccharide solution was further purified by filtration through a depth filter impregnated with activated carbon. After filtration, the carbon filter was rinsed with a sodium chloride solution. The rinse was combined with the polysaccharide solution, which was then filtered through a 0.2 μm filter.

The polysaccharide solution was concentrated on a 30 kDa MWCO ultrafilter and the filter was rinsed with a sodium chloride solution. The pH was checked and adjusted to 7.0±0.3.

The ceramic hydroxyapatite (HA) column was equilibrated with sodium phosphate buffer containing sodium chloride until the pH is 7.0±0.3 and the conductivity was 26±4 μS. The polysaccharide solution was then loaded onto the column. Under these conditions, impurities bound to the resin and the polysaccharide was recovered in the flow through from the column. The polysaccharide solution was filtered through a 0.2 μm filter.

The polysaccharide solution was concentrated using a 30 kDa MWCO filter. The concentrate was then diafiltered with WFI until the conductivity was <15 μS.

The diafiltered polysaccharide solution was filtered through a 0.2 μm membrane filter into bulk containers and stored at 2-8° C.

Example 14

Preparation of Pneumococcal Saccharide-CRM$_{197}$ Conjugates for Serotypes 4, 6B, 9V, 14, 18C, 19F and 23F Activation Process The different serotype saccharides follow different pathways for activation (hydrolysis or no hydrolysis prior to activation) and conjugation (aqueous or DMSO reactions) as described in this example.

Polysaccharide was transferred from the bulk containers to the reactor vessel. The polysaccharide was then diluted in WFI and sodium phosphate to a final concentration range of 1.6-2.4 mg/mL.

Step 1.

For serotypes 6B, 9V, 14, 19F and 23F, pH was adjusted to pH 6.0±0.3.

For serotype 4, hydrochloric acid (0.01 M final acid concentration) was added and the solution was incubated for 25-35 minutes at 45°±2° C. Hydrolysis was stopped by cooling to 21-25° C. and adding 1M sodium phosphate to a target of pH 6.7±0.2. An in-process test was done to confirm an appropriate level of depyruvylation.

For serotype 18C, glacial acetic acid (0.2 M final acid concentration) was added and the solution was incubated for 205-215 minutes at 94°±2° C. Temperature was then decreased to 21-25° C. and 1-2 M sodium phosphate was added to a target of pH 6.8±0.2.

Step 2: Periodate Reaction

The required sodium periodate molar equivalents for pneumococcal saccharide activation was determined using total saccharide content (except for serotype 4). For serotype 4, a ratio of 0.8-1.2 moles of sodium periodate per mole of saccharide was used. With thorough mixing, the oxidation reaction was allowed to proceed between 16 to 20 hours at 21-25° C. for all serotypes except 19F for which the temperature was ≤15° C.

Step 3: Ultrafiltration

The oxidized saccharide was concentrated and diafiltered with WFI (0.01 M sodium phosphate buffer pH 6.0 for serotype 19F) on a 100 kDa MWCO ultrafilter (5 kDa ultrafilter for 18C). The permeate was discarded and the retentate was filtered through a 0.22 μm filter.

Step 4: Lyophilization

For serotypes 4, 9V, and 14 the concentrated saccharide was mixed with CRM$_{197}$ carrier protein, filled into glass bottles, shell-frozen and stored at ≤−65° C. The frozen concentrated saccharide-CRM$_{197}$ was lyophilized and then stored at −25°±5° C.

For serotypes 6B, 19F, and 23F a specified amount of sucrose was added which was calculated to achieve a 5%±3% sucrose concentration in the conjugation reaction mixture. Serotype 18C did not require sucrose addition. The concentrated saccharide was then filled into glass bottles, shell-frozen and stored at ≤−65° C. The frozen concentrated saccharide was lyophilized and then stored at −25°±5° C.

Conjugation Process

Two conjugation processes were used: aqueous conjugation for serotypes 4, 9V, 14 and 18C, and DMSO conjugation for serotypes 6B, 19F and 23F.

Aqueous Conjugation

Step 1: Dissolution

For serotypes 4, 9V and 14, the lyophilized activated saccharide-CRM$_{197}$ mixture was thawed and equilibrated at room temperature. The lyophilized activated saccharide-CRM$_{197}$ was then reconstituted in 0.1M sodium phosphate buffer at a typical ratio of:

1 L of buffer per 16-24 g of saccharide for serotype 4 and 9V

1 L of buffer per 6-10 g of saccharide for serotype 14

The reaction mixture was incubated at 37°±2° C. until total dissolution for the serotype 9V and at 23°±2° C. for serotypes 4 and 14.

For serotype 18C, the lyophilized saccharide was reconstituted in a solution of CRM$_{197}$ in 1M dibasic sodium phosphate at a typical ratio of 0.11 L of sodium phosphate per 1 L of CRM$_{197}$ solution. The reaction mixture (8-12 g/L saccharide concentration) was incubated at 23°±2° C. until total dissolution.

The pH was tested as an in-process control at this stage.

Step 2: Conjugation Reaction

For serotypes 4 and 9V, the conjugation reaction was initiated by adding the sodium cyanoborohydride solution (100 mg/mL) to achieve 1.0-1.4 moles sodium cyanoborohydride per mole of saccharide. The reaction mixture was incubated for 44-52 hours at 37°±2° C. The temperature was then reduced to 23°±2° C. and sodium chloride 0.9% was added to the reactor. Sodium borohydride solution (100 mg/mL) was added to achieve 1.8-2.2 molar equivalents of sodium borohydride per mole saccharide. The mixture was incubated for 3-6 hours at 23°±2° C. The mixture was diluted with sodium chloride 0.9% and the reactor was rinsed. The diluted conjugation mixture was filtered using a 1.2 μm pre-filter into a holding vessel.

For serotypes 14 and 18C, the conjugation reaction was initiated by adding the cyanoborohydride solution (100 mg/mL) to achieve 1.0-1.4 moles of sodium cyanoborohydride per mole of saccharide. The reaction mixture was incubated for 12-24 hours at 23°±2° C. The temperature was increased to 37°±2° C. and the reaction was incubated for 72-96 hours. The temperature was then reduced to 23° ±2° C. and 0.9% sodium chloride was added to the reactor. Sodium borohydride solution (100 mg/mL) was added to achieve 1.8-2.2 molar equivalents of sodium borohydride per mole of saccharide. The mixture was incubated for 3-6 hours at 23°±2° C. The mixture was diluted with 0.9% sodium chloride and the reactor was rinsed. The diluted conjugation mixture was then filtered using a 1.2 μm pre-filter into a holding vessel.

Step 3: Ultrafiltration 100 kDa

The diluted conjugation mixture was concentrated and diafiltrated on a 100 kDa MWCO ultrafilter with either a minimum of 15 volumes (serotype 4) or 40 volumes (serotypes 9V, 14, and 18C) of 0.9% sodium chloride.

The permeate was discarded.

For serotype 4, the retentate was filtered through a 0.45 μm filter.

An in-process control (saccharide content) was performed at this step.

Step 4: HA Column Purification

This step was only performed for the serotype 4 conjugate.

The HA column was first neutralized using 0.5M sodium phosphate buffer (pH 7.0±0.3) and then equilibrated with 0.9% sodium chloride. The filtered retentate (serotype 4) was loaded onto the column at a flow rate of 1.0 L/min. The column was washed with 0.9% sodium chloride at a flow rate of ≤2.0 L/min. The product was then eluted with 0.5M sodium phosphate buffer at a flow rate of ≤2.0 L/min.

The HA fraction was then concentrated and diafiltered on a 100 kDa MWCO membrane with a minimum of 20 volumes of 0.9% sodium chloride. The permeate was discarded.

Step 5: Sterile Filtration

The retentate after the 100 kDa MWCO diafiltration was filtered through a 0.22 µm filter. In-process controls (saccharide content, free protein, free saccharide and cyanide) were performed on the filtered product. In-process controls on filtered retentate were performed to determine whether additional concentration, diafiltration, and/or dilution were needed to meet FBC targets. These and additional tests were repeated in FBC samples.

As necessary, the filtered conjugate was diluted with 0.9% sodium chloride in order to achieve a final concentration of less than 0.55 g/L. Release tests for saccharide content, protein content and saccharide:protein ratio were performed at this stage.

Finally, the conjugate was filtered (0.22 µm) and filled into 10 L stainless steel canisters at a typical quantity of 2.64 g/canister. At this stage, yield, saccharide content, protein content, pH, saccharide:protein ratio and lysine content were performed as in-process controls. Release testing (appearance, free protein, free saccharide, endotoxin, molecular size determination, residual cyanide, saccharide identity, $CRM_{197}$ identity) was performed at this stage.

DMSO Conjugation

Step I: Dissolution

The lyophilized activated saccharide serotypes 6B, 19F, 23F and the lyophilized $CRM_{197}$ carrier protein were equilibrated at room temperature and reconstituted in DMSO. The dissolution concentration typically ranged from 2-3 grams of saccharide (2-2.5 g protein) per liter of DMSO.

Step II: Conjugation Reaction

The activated saccharide and $CRM_{197}$ carrier protein were mixed for 60-75 minutes at 23°±2° C. at a ratio range of 0.6 g-1.0 g saccharide/g $CRM_{197}$ for serotypes 6B and 19F or 1.2 to 1.8 g saccharide/g $CRM_{197}$ for serotype 23F.

The conjugation reaction was initiated by adding the sodium cyanoborohydride solution (100 mg/mL) at a ratio of 0.8-1.2 molar equivalents of sodium cyanoborohydride to one mole activated saccharide. WFI was added to the reaction mixture to a target of 1% (v/v) and the mixture was incubated for over 40 hours at 23°±2° C.

Sodium borohydride solution, 100 mg/mL (typical 1.8-2.2 molar equivalents sodium borohydride per mole activated saccharide) and WFI (target 5% v/v) were added to the reaction and the mixture was incubated for 3-6 hours at 23°±2° C. This procedure reduced any unreacted aldehydes present on the saccharides. Then the reaction mixture was transferred to a dilution tank containing 0.9% sodium chloride at <15° C.

Step III: 100 kDa Ultrafiltration

The diluted conjugate mixture was filtered through a 1.2 µm filter and concentrated and diafiltered on a 100 kDa MWCO membrane with a minimum of 15 volumes of 0.9% sodium chloride (0.01M sodium phosphate/0.05M NaCl buffer was used for serotype 23F). The permeate was discarded. The retentate was filtered through a 0.45 µm filter. An in-process saccharide content sample was taken at this stage.

Step IV: DEAE Column Purification

This step was only performed for serotype 23F.

The DEAE column was equilibrated with 0.01M sodium phosphate/0.05M sodium chloride buffer. The filtered retentate (serotype 23F) was loaded onto the column and washed with 0.01M sodium phosphate/0.05M sodium chloride buffer. The column was then washed with 0.01M sodium phosphate/0.9% NaCl buffer. The product was then eluted with 0.01M sodium phosphate/0.5M sodium chloride buffer.

Step V: 100 kDa Ultrafiltration

The retentate from 6B and 19F was concentrated and diafiltered with at least 30 volumes of 0.9% sodium chloride. The permeate was discarded.

The eluate from serotype 23F was concentrated and diafiltered with a minimum of 20 volumes of 0.9% sodium chloride. The permeate was discarded.

Step VI: Sterile Filtration

The retentate after the 100 kDa MWCO dialfiltration was filtered through 0.22 µm filter. In-process controls (saccharide content, free protein, free saccharide, residual DMSO and residual cyanide) were performed on the filtered product. In-process controls on filtered retentate were performed to determine whether additional concentration, diafiltration, and/or dilution were needed to meet FBC targets. These and additional tests were repeated in FBC samples.

As necessary, the filtered conjugate was diluted with 0.9% sodium chloride to achieve a final concentration of less than 0.55 g/L. Release tests for saccharide content, protein content and saccharide:protein ratio were performed at this stage.

Finally, the conjugate was filtered (0.22 µm) and filled into 10 L stainless steel canisters at a quantity of 2.64 g/canister. At this stage, yield, saccharide content, protein content, pH, saccharide:protein ratio and lysine content were performed as in-process controls. Release testing (appearance, free protein, free saccharide, endotoxin, molecular size determination, residual cyanide, residual DMSO, saccharide identity and $CRM_{197}$ identity) was performed at this stage.

Example 15

Formulation of a Multivalent Pneumococcal Conjugate Vaccine

The final bulk concentrates of the 13 conjugates contain 0.85% sodium chloride. Type 3, 6A, 7F and 19A bulk concentrates also contain 5 mM sodium succinate buffer at pH 5.8. The required volumes of bulk concentrates were calculated based on the batch volume and the bulk saccharide concentrations. After 80% of the 0.85% sodium chloride (physiological saline) and the required amount of succinate buffer were added to the pre-labeled formulation vessel, bulk concentrates were added. The preparation was then sterile filtered through a 0.22 µm membrane into a second container by using a Millipore Durapore membrane filter unit. The first container was washed with the remaining 20% of 0.85% sodium chloride and the solution was passed through the same filter and collected into the second container. The formulated bulk was mixed gently during and following the addition of bulk aluminum phosphate. The pH was checked and adjusted if necessary. The formulated bulk product was stored at 2-8° C.

The formulated bulk product was filled into Type 1 borosilicate glass syringes obtained from Becton Dickinson. The vaccine was monitored at regular intervals for turbidity to ensure the uniformity of the filling operation. The filled vaccine (Final Product) was stored at 2-8° C.

Example 16

Immunogenicity of the 13-Valent Conjugate Vaccine

To date, the preclinical studies performed on the 13vPnC vaccine have been in rabbits. Studies #HT01-0021 and #HT01-0036 were designed to independently examine the effect of chemical conjugation of capsular polysaccharides (PSs) from S. pneumoniae to $CRM_{197}$ and the effect of aluminum phosphate ($AlPO_4$) adjuvant on the immune response to the 13vPnC vaccine in rabbits. These effects were characterized by antigen-specific ELISA for serum IgG concentrations and for antibody function by opsonophagocytic assay (OPA).

Study #HT01-0021

Study #HT01-0021 examined the ability of the 13vPnC vaccine with $AlPO_4$ adjuvant to elicit vaccine serotype-specific immune responses. The pneumococcal serotypes represented in the 13vPnC vaccine include types 1, 3, 4, 5, 6A, 6B, 7F, 9V, 14, 18C, 19A, 19F and 23F. Secondary objectives included an evaluation of the kinetics and duration of the antibody response. New Zealand White rabbits were immunized intramuscularly at week 0 and week 2 with the planned human clinical dose of each polysaccharide (2 µg of each PS, except 4 µg of 6B) formulated with or without $AlPO_4$ (100 µg/dose). Sera were collected at various time points. Serotype specific IgG was measured by ELISA and functional activity was assessed by OPA.

Table 3 shows the geometric mean titer (GMT) achieved in pooled serum samples, following two doses of the 13vPnC vaccine. A ratio of the IgG GMTs was used to compare responses from week 4 to week 0. These data demonstrate that the inclusion of $AlPO_4$ in the 13vPnC formulation elicited higher levels of IgG antibody in comparison to the same vaccine without adjuvant. Although the antibody responses were greater when $AlPO_4$ was included in the formulation, these increases were not statistically significant.

Functional antibody responses were also assessed in rabbits following immunization with the two 13vPnC formulations (Table 4). When comparing vaccine formulations with or without adjuvant, higher OPA GMTs were observed in the 13vPnC+$AlPO_4$ vaccine treatment group. OPA titers were detected in week 4 serum pools to all vaccine serotypes in both groups. For the majority of the serotypes, OPA titers measured at week 4 were at least 4-fold higher than those at week 0 (baseline).

The kinetic responses to each of the 13vPnC vaccine serotypes were evaluated from serum pools of both treatment groups. IgG titers to each serotype were measured from blood draws at week 0 and weeks 1, 2, 3, 4, 8, 12, 26, and 39 and then compared. With the exception of serotype 1, antibody responses in animals receiving adjuvanted vaccine were superior to those that received non-adjuvanted vaccine and peaked at week 2 of the immunization schedule (data not shown).

Overall, the data indicate that the 13vPnC vaccine formulated with aluminum phosphate is immunogenic in rabbits, eliciting substantial antibody responses to the pneumococcal capsular polysaccharides contained in the vaccine and these responses are associated with functional activity. The responses observed to the seven core serotypes following immunization with 13vPnC+$AlPO_4$ are consistent with historical responses of rabbits to the heptavalent formulation.

TABLE 3

Rabbit IgG Immune Responses (GMTs) Following Immunization with Two Doses of 13-valent Pneumococcal Glycoconjugate

| | Diluent with $ALPO_4$[a] | | | 13vPnC[a] | | | 13vPnC + $ALPO_4$[a] | | |
| --- | --- | --- | --- | --- | --- | --- | --- | --- | --- |
| Serotype | Week 0 | Week 4 | Ratio Wk 4:Wk 0 | Week 0 | Week 4 (95% CI) | Ratio Wk 4:Wk 0 | Week 0 | Week 4 (95% CI) | Ratio Wk 4:Wk 0 |
| 1 | <100 | <100 | 1.0 | 50 | 5,926 (2,758-12,733) | 119 | 50 | 11,091 (5,327-23,093) | 222 |
| 3 | <100 | <100 | 1.0 | 50 | 6,647 (2,773-15,932) | 133 | 58 | 16,443 (7,096-38,106) | 284 |
| 4 | <100 | <100 | 1.0 | 50 | 13,554 (8,031-22,875) | 271 | 50 | 29,183 (15,342-55,508) | 584 |
| 5 | 134 | <100 | 0.4 | 50 | 5,859 (2,450-14,009) | 117 | 50 | 16,714 (6,959-40,140) | 334 |
| 6A | 141 | <100 | 0.4 | 74 | 22,415 (11,987-41,914) | 303 | 83 | 63,734 (21,141-192,146) | 768 |
| 6B | <100 | <100 | 1.0 | 57 | 8,108 (3,564-18,444) | 142 | 54 | 23,505 (11,286-48,955) | 435 |
| 7F | 3,859 | 579 | 0.2 | 171 | 43,591 (26,931-70,557) | 444 | 143 | 84,888 (46,445-155,151) | 496 |
| 9V | 289 | 995 | 3.4 | 205 | 15,780 (7,193-34,616) | 125 | 208 | 43,331[b] (23,256-71,510) | 217 |
| 14 | 437 | 177 | 0.4 | 61 | 6,906 (3,416-13,962) | 113 | 70 | 16,076 (9,649-26,785) | 322 |
| 18C | <100 | <100 | 1.0 | 50 | 21,283 (15,770-28,725) | 426 | 50 | 35,040 (24,708-49,692) | 701 |
| 19A | <100 | <100 | 1.0 | 121 | 113,599 (54,518-236,707) | 939 | 144 | 280,976 (119,587-660,167) | 1,951 |
| 19F | <100 | <100 | 1.0 | 50 | 14,365 (7,346-28,090) | 287 | 50 | 24,912 (9,243-67,141) | 498 |
| 23F | <100 | <100 | 1.0 | 50 | 5,323 (1,894-14,962) | 106 | 50 | 15,041 (4,711-48,018) | 301 |

[a]GMTs of pooled sera consisted of equal volumes of serum from each individual rabbit within a group
[b]Statistically different (p = 0.022) from treatment group without $ALPO_4$

TABLE 4

S. pneumoniae OPA GMTs for NZW Rabbit Serum Pools Following Immunization with Two Doses of 13-valent Pneumococcal Glycoconjugate

| | 13vPnC[a] | | | 13vPnC + ALPO$_4$[a] | | |
|---|---|---|---|---|---|---|
| Serotype | Week 0 | Week 4 | Ratio Wk 4:Wk 0 | Week 0 | Week 4 | Ratio Wk 4:Wk 0 |
| 1 | <8 | 64 | 16 | <8 | 64 | 16 |
| 3 | <8 | 8 | 2 | <8 | 16 | 4 |
| 4 | <8 | 16 | 4 | <8 | 32 | 8 |
| 5 | <8 | 128 | 32 | <8 | 512 | 128 |
| 6A | 8 | 128 | 16 | 8 | 512 | 64 |
| 6B | <8 | 256 | 64 | 8 | 1,024 | 128 |
| 7F | 8 | 64 | 8 | 8 | 128 | 16 |
| 9V | 8 | 64 | 8 | 8 | 128 | 16 |
| 14 | 16 | 32 | 2 | 16 | 32 | 2 |
| 18C | 8 | 256 | 32 | <8 | 256 | 64 |
| 19A | <8 | 256 | 64 | <8 | 1,024 | 256 |
| 19F | <8 | 128 | 32 | <8 | 512 | 128 |
| 23F | 8 | 64 | 8 | <8 | 256 | 64 |

[a]Pools consisted of equal volumes of serum from individual rabbits within a treatment group (n = 12)

Study #HT01-0036

Study #HT01-0036 compared rabbit immune responses to the polysaccharides (PSs) contained in the vaccine, after immunization with the 13vPnC vaccine with or without conjugation to the $CRM_{197}$ protein. New Zealand White rabbits were immunized intramuscularly at week 0 and week 2 with a dose of 2.2 µg of each PS (except 4.4 µg of 6B). Animals received one of three vaccine preparations: (a) 13vPnC (PS directly conjugated to $CRM_{197}$), (b) 13vPnPS, (free PS) or (c) 13vPnPS+$CRM_{197}$ (free PS mixed with $CRM_{197}$). All vaccine preparations contained $AlPO_4$ as the adjuvant at 125 µg/dose.

Serotype specific immune responses for all vaccine preparations were evaluated in an IgG ELISA and complement-mediated OPA measuring functional antibody. The immune responses were compared between the treatment groups.

Table 5 presents GMT data obtained from week 4 bleeds analyzed in antigen specific IgG ELISAs. Additional analyses show the ratio of GMT values at week 4 to week 0. The data indicate that the conjugate vaccine preparation elicited greater serum IgG titers than free PS or free PS+$CRM_{197}$ vaccine. With the exception of S. pneumoniae type 14, the 13vPnC vaccine was able to induce functional antibodies to the representative strains of S. pneumoniae in an OPA (Table 6). After two immunizations with either the 13vPnPS or 13vPnPS+$CRM_{197}$ vaccine, neither could induce OPA titers ≥8-fold at week 4 relative to week 0 for 10 out of the 13 serotypes measured (Table 6).

In conclusion, these results indicate that conjugation of the 13-valent pneumococcal vaccine polysaccharides produces higher serum IgG titers and overall greater functional antibody activity than seen with free polysaccharide alone or mixed with unconjugated $CRM_{197}$.

TABLE 5

Rabbit IgG Responses (GMTs) to PnPS by ELISA Following Immunization with Two Doses of 13-valent Pneumococcal Glycoconjugate

| | 13vPnPS (free PS) | | | 13vPnPS = $CRM_{197}$ (PS mixed with $CRM_{197}$) | | | 13vPnC | | |
|---|---|---|---|---|---|---|---|---|---|
| Serotype | Week 0 | Week 4 (95% CI) | Ratio Wk 4:Wk 0 | Week 0 | Week 4 (95% CI) | Ratio Wk 4:Wk 0 | Week 0 | Week 4 (95% CI) | Ratio Wk 4:Wk 0 |
| 1 | 378 | 2,290 (843-5,790) | 5.8 | 395 | 1,959 (809-4,739) | 5.0 | 472 | 35,970 (29,130-44,417) | 76.2 |
| 3 | 57 | 240 (64-908) | 4.2 | 89 | 163 (74-358) | 1.8 | 50 | 10,414 (10,414-16,676) | 208.3 |
| 4 | 50 | 379 (150-959) | 7.6 | 50 | 607 (313-1,178) | 12.1 | 50 | 12,890 (9,117-18,224) | 257.8 |
| 5 | 343 | 226 (113-450) | 4.5 | 50 | 321 (147-701) | 6.4 | 50 | 35,264 (24,467-50,824) | 705.3 |
| 6A | 154 | 466 (316-688) | 3.0 | 98 | 210 (95-464) | 2.1 | 163 | 234,245 (167,152-328,283) | 1,437.1 |
| 6B | 63 | 727 (384-1,375) | 11.6 | 62 | 745 (384-1,440) | 12.0 | 131 | 33,599 (22,934-49,222) | 256.5 |
| 7F | 50 | 61 (39-95) | 1.2 | 50 | 72 (47-111) | 1.4 | 50 | 35,702 (24,350-52,347) | 714.0 |
| 9V | 50 | 104 (48-195) | 2.1 | 55 | 169 (74-390) | 3.0 | 50 | 50,033 (34,765-72,007) | 1,000.7 |
| 14 | 66 | 298 (117-757) | 4.5 | 50 | 195 (71-535) | 3.9 | 50 | 20,121 (12,087-32,138) | 402.4 |
| 18C | 89 | 1,555 (655-3,688) | 17.5 | 66 | 761 (300-1,935) | 11.5 | 101 | 71,451 (32,745-124,641) | 707.4 |
| 19A | 50 | 89 (44-179) | 1.8 | 50 | 80 (39-163) | 1.6 | 50 | 23,485 (12,857-42,723) | 469.7 |

TABLE 5-continued

Rabbit IgG Responses (GMTs) to PnPS by ELISA Following Immunization with Two Doses of 13-valent Pneumococcal Glycoconjugate

| | 13vPnPS (free PS) | | | 13vPnPS = $CRM_{197}$ (PS mixed with $CRM_{197}$) | | | 13vPnC | |
|---|---|---|---|---|---|---|---|---|
| Serotype | Week 0 | Week 4 (95% CI) | Ratio Wk 4:Wk 0 | Week 0 | Week 4 (95% CI) | Ratio Wk 4:Wk 0 | Week 0 | Week 4 (95% CI) | Ratio Wk 4:Wk 0 |
| 19F | 61 | 1,362 (559-3,317) | 22.3 | 61 | 991 (370-2,654) | 16.3 | 67 | 19,358 (12,553-33,173) | 288.9 |
| 23F | 73 | 1,085 (487-2,420) | 14.9 | 121 | 638 (311-1,311) | 5.3 | 68 | 45,972 (25,134-84,089) | 676.1 |

TABLE 6

*S. pneumoniae* OPA Titers for Rabbit Serum Pools Following Immunization with Two Doses of 13-valent Pneumococcal Vaccines

| | OPA Titers | | | | | | |
|---|---|---|---|---|---|---|---|
| | No Treatment | 13vPnPS (free PS) | | 13vPnPS + $CRM_{197}$ (free PS mixed with $CRM_{197}$) | | 13vPnC | |
| Serotype | Week $0^a$ | Week 4 | Ratio Wk 4:Wk 0 | Week 4 | Ratio Wk 4:Wk 0 | Week 4 | Ratio Wk 4:Wk 0 |
| 1 | 4 | 16 | 4 | 16 | 4 | 128 | 32 |
| 3 | 4 | 4 | 1 | 4 | 1 | 32 | 8 |
| 4 | 4 | 4 | 1 | 4 | 1 | 256 | 64 |
| 5 | 4 | 32 | 8 | 16 | 4 | 256 | 64 |
| 6A | 8 | 64 | 8 | 32 | 4 | 512 | 664 |
| 6B | 8 | 64 | 8 | 32 | 4 | 256 | 32 |
| 7F | 16 | 32 | 2 | 16 | 1 | 256 | 16 |
| 9V | 16 | 16 | 1 | 32 | 2 | 128 | 8 |
| 14 | 16 | 16 | 1 | 16 | 1 | 32 | 2 |
| 18C | 4 | 16 | 4 | 16 | 4 | 256 | 64 |
| 19A | 8 | 8 | 1 | 8 | 1 | 512 | 64 |
| 19F | 4 | 4 | 1 | 4 | 1 | 256 | 64 |
| 23F | 16 | 32 | 2 | 16 | 1 | 512 | 32 |

$^a$Used as week 0 values for all groups

It should be understood that the foregoing discussion and examples merely present a detailed description of certain embodiments. It therefore should be apparent to those of ordinary skill in the art that various modifications and equivalents can be made without departing from the spirit and scope of the invention.

All journal articles, other references, patents and patent applications that are identified in this patent application are incorporated by reference in their entirety.

REFERENCES

1. Hausdorff W P, Bryant J, Paradiso P R, Siber G R. Which pneumococcal serogroups cause the most invasive disease: implications for conjugate vaccine formulation and use, part I. *Clin Infect Dis* 2000; 30:100-21.
2. Hausdorff W P, Bryant J, Kloek C, Paradiso P R, Siber G R. The contribution of specific pneumococcal serogroups to different disease manifestations: implications for conjugate vaccine formulation and use, part I. *Clin Infect Dis* 2000; 30:122-40.
3. Whitney C G, Farley M M, Hadler J, et al. Decline in invasive pneumococcal disease after the introduction of protein-polysaccharide conjugate vaccine. *New Engl J Med* 2003; 348(18):1737-46.
4. Black S, Shinefield H, Hansen J, et al. Postlicensure evaluation of the effectiveness of seven valent pneumococcal conjugate vaccine. *Pediatr Infect Dis J* 2001; 20; 1105-7.
5. Robinson K A, Baughman W, Rothrock G, et al. Epidemiology of invasive *Streptococcus pneumoniae* infections in the United States, 1995-1998: Opportunities for prevention in the conjugate vaccine era. *JAMA* 2001; 285: 1729-35.
6. Butler J, Breiman R, Lipman H, et al. Serotype distribution of *Streptococcus pneumoniae* infections among preschool children in the United States, 1978-1994. *J Infect Dis* 1995; 171:885-9.
7. Whitney C G, Farley M M, Hadler J, et al. Increasing prevalence of multidrug-resistant *Streptococcus pneumoniae* in the United States. *N Engl J Med* 2000; 343:1917-24.
8. Hofmann J, Cetron M S, Farley M M, et al. The prevalence of drug-resistant *Streptococcus pneumoniae* in Atlanta. *N Engl J Med* 1995; 333:481-6.
9. Joloba M L, Windau A, Bajaksouzian S, Appelbaum P C Hausdorff W P, Jacobs M R. Pneumococcal conjugate vaccine serotypes of *Streptococcus pneumoniae* isolates and the antimicrobial susceptibility of such isolates in children with otitis media. *Clin Infect Dis* 2001; 33:1489-94.
10. Black S, Shinefield H, Fireman B, et al. Efficacy, safety, and immunogenicity of heptavalent pneumococcal conjugate vaccine in children. *Pediatr Infect Dis J* 2000; 19:187-95.
11. Rudolph K M, Parkinson A J, Reasonover A L, Bulkow L R, Parks D J, Butler J C. Serotype distribution and antimicrobial resistance patterns of invasive isolates of *Streptococcus pneumoniae*: Alaska, 1991-1998. *J Infect Dis* 2000; 182:490-6.
12. Sniadack D H, Schwartz B, Lipman H, et al. Potential interventions for the prevention of childhood pneumonia: geographic and temporal differences in serotype and serogroup distribution of sterile site pneumococcal isolates from children: implications for vaccine strategies. *Pediatr Infect Dis J* 1995; 14:503-10.
13. Fagan R L, Hanna J N, Messer R D, Brookes D L, Murphy D M. The epidemiology of invasive pneumococcal disease in children in Far North Queensland. *J. Paediatr Child Health* 2001; 37:571-5.
14. Kertesz D A, Di Fabio J L, de Cunto Brandileone M C, et al. Invasive *Streptococcus pneumoniae* infection in Latin American children: results of the Pan American Health Organization Surveillance Study. *Clin Infect Dis* 1998; 26:1355-61.
15. Hausdorff W, Siber G, Paradiso P. Geographical differences in invasive pneumococcal disease rates and serotype frequency in young children. *Lancet* 2001; 357:950-52.
16. Buckingham S C, King M D, Miller M L. Incidence and etiologies of complicated parapneumonic effusions in children, 1996 to 2001. *Pediatr Infect Dis J* 2003; 22:499-504.
17. Byington C, Spencer L, Johnson T, et al. An epidemiological investigation of a sustained high rate of pediatric parapneumonic empyema: risk factors and microbiological associations. *Clin Infect Dis* 2002; 34:434-40.
18. Tan T, Mason E, Wald E, et al. Clinical characteristics with complicated pneumonia caused by *Streptococcus pneumoniae*. *Pediatrics* 2002; 110:1-6.
19. Block S L, Hedrick J, Harrison C J, et al. Pneumococcal serotypes from acute otitis media in rural Kentucky. *Pediatr Infect Dis J* 2002; 21:859-65.
20. Hausdorff W P, Yothers G, Dagan R, et al. Multinational study of pneumococcal serotypes causing acute otitis media in children. *Pediatr Infect Dis J* 2002; 21:1008-16.
21. Robbins J B, Austrian R, Lee C J, et al. Considerations for formulating the second-generation pneumococcal capsular polysaccharide vaccine with emphasis on the cross-reactive types within groups. *J Infect Dis* 1983; 148:1136-59.
22. Nahm M H, Olander J V, Magyarlaki M. Identification of cross-reactive antibodies with low opsonophagocytic activity for *Streptococcus pneumoniae*. *J Infect Dis* 1997; 176:698-703.
23. Yu X, Gray B, Chang S, Ward J I, Edwards K M, Nahm M H. Immunity to cross-reactive serotypes induced by pneumococcal conjugate vaccines in infants. *J Infect Dis* 1999; 180:1569-76.
24. Vakevainen M, Eklund C, Eskola J, Kayhty H. Cross-reactivity of antibodies to type 6B and 6A polysaccharides of *Streptococcus pneumoniae*, evoked by pneumococcal conjugate vaccines, in infants. J Infect Dis 2001; 184:789-93.
25. Ekstrom N, Kilpi T, Landenkari M, Lehtonen H, Ahman H, Kayhty, H. Immune response to cross-reacting pneumococcal serotypes 6A/6B and 19A/19F in the FinOM vaccine trial, Third World of Congress of Pediatric Infectious Diseases, Santiago, Chile, Nov. 19-23, 2003.
26. Penn R L, Lewin E B, Douglas R G, Jr., Schiffman G, Lee C J, Robbins J B. Antibody responses in adult volunteers to pneumococcal polysaccharide types 19F and 19A administered singly and in combination. *Infect Immun* 1982; 36:1261-2.
27. Giebink G S, Meier J D, Quartey M K, Liebeler C L, Le C T. Immunogenicity and efficacy of *Streptococcus pneumoniae* polysaccharide-protein conjugate vaccines against homologous and heterologous serotypes in the chinchilla otitis media model. *J Infect Dis* 1996; 173:119-27.
28. Saeland E, Jakobsen H, Ingolfsdottir G, Sigurdardottir S T, Jonsdottir I. Serum samples from infants vaccinated with a pneumococcal conjugate vaccine, PncT, protect mice against invasive infection caused by *Streptococcus pneumoniae* serotypes 6A and 6B. *J Infect Dis* 2001; 183:253-60.
29. Jakobsen H, Sigurdsson V D, Sigurdardottir S, Schulz D, Jonsdottir I. Pneumococcal serotype 19F conjugate vaccine induces cross-protective immunity in serotype 19A in a murine pneumococcal pneumonia model. *Infect Immun* 2003; 71:2956-9.
30. Klugman K P, Madhi S A, Huebner R E, Kohberger R, Mbelle N, Pierce N. A trial of a 9-valent pneumococcal conjugate vaccine in children with and those without HIV infection. *N Engl J Med* 2003; 349:1341-8.
31. O'Brien K L, Moulton L H, Reid R, et al. Efficacy and safety of seven-valent conjugate pneumococcal vaccine in American Indian children: group randomised trial. *Lancet* 2003; 362:355-61.
32. Eskola J, Kilpi T, Palmu A, et al. Efficacy of a pneumococcal conjugate vaccine against acute otitis media. *N Engl J Med* 2001: 344:403-9.
33. Pilishvili T, Farley M, Vazquez M, Reingold A, Nyquist A, et al. Effectiveness of heptavalent pneumococcal conjugate vaccine in children. Abst G-1079, ICAAC, Chicago, Ill., 2003.
34. U.S. Pat. No. 4,673,574.
35. U.S. Pat. No. 4,902,506.

What is claimed is:

1. A method for making an immunogenic conjugate comprising *Streptococcus pneumoniae* serotype 4 polysaccharide covalently linked to a carrier protein, the method comprising: (a) reacting purified serotype 4 polysaccharide with a mild hydrochloric acid to yield hydrolyzed serotype 4 polysaccharide; (b) reacting the hydrolyzed serotype 4 polysaccharide with an oxidizing agent, wherein the oxidizing agent is periodic acid to yield activated serotype 4 polysaccharide; (c) compounding and co-lyophilizing the activated serotype 4 polysaccharide with a $CRM_{197}$ carrier protein; (d) reacting the co-lyophilized, activated serotype 4 polysaccharide and $CRM_{197}$ carrier protein with sodium cyanoborohydride to yield serotype 4 polysaccharide: $CRM_{197}$ carrier protein conjugate; and (e) capping unreacted aldehydes in the serotype 4 polysaccharide: $CRM_{197}$ carrier protein conjugate with sodium borohydride to yield an immunogenic conjugate comprising *Streptococcus pneumoniae* serotype 4 polysaccharide covalently linked to a $CRM_{197}$ carrier protein.

2. The method of claim 1, further comprising purifying the immunogenic conjugate.

3. A method for making an activated *Streptococcus pneumoniae* serotype 4 polysaccharide, the method comprising: (a) reacting purified serotype 4 polysaccharide with a mild hydrochloric acid to yield a hydrolyzed serotype 4 polysaccharide; and (b) reacting the hydrolyzed serotype 4 polysaccharide with an oxidizing agent wherein the oxidizing agent is periodic acid to yield activated serotype 4 polysaccharide.

4. The method of claim 3, further comprising purifying the activated serotype 4 polysaccharide following oxidation.

* * * * *